(12) United States Patent
Chan

(10) Patent No.: US 8,586,375 B2
(45) Date of Patent: *Nov. 19, 2013

(54) RAPID DIAGNOSTIC DEVICE, ASSAY AND MULTIFUNCTIONAL BUFFER

(75) Inventor: Hermes K. W. Chan, Halifax (CA)

(73) Assignee: MedMira Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/610,151

(22) Filed: Sep. 11, 2012

(65) Prior Publication Data

US 2013/0040286 A1 Feb. 14, 2013

Related U.S. Application Data

(60) Continuation of application No. 13/243,293, filed on Sep. 23, 2011, now Pat. No. 8,287,817, which is a division of application No. 12/285,868, filed on Oct. 15, 2008, now Pat. No. 8,025,850, which is a continuation of application No. 10/163,675, filed on Jun. 6, 2002, now Pat. No. 7,531,362.

(60) Provisional application No. 60/296,147, filed on Jun. 7, 2001, provisional application No. 60/309,477, filed on Aug. 3, 2001.

(51) Int. Cl.
*G01N 33/48* (2006.01)

(52) U.S. Cl.
USPC ........... 436/164; 436/166; 436/169; 422/401; 422/420; 422/430

(58) Field of Classification Search
USPC ........... 422/401, 420, 430; 436/164, 166, 169
See application file for complete search history.

(56) References Cited

U.S. PATENT DOCUMENTS

| | | | |
|---|---|---|---|
| 4,087,567 | A | 5/1978 | Sullivan |
| 4,094,647 | A | 6/1978 | Deutsch et al. |
| 4,168,146 | A | 9/1979 | Grubb et al. |
| 4,235,601 | A | 11/1980 | Deutsch et al. |
| 4,361,537 | A | 11/1982 | Deutsch et al. |
| 4,446,232 | A | 5/1984 | Liotta |

(Continued)

OTHER PUBLICATIONS

Original of MedMira Laboratories Inc., MedMira Rapid HIV Test Kit Serum or Plasma Testing, 2000, ad for worldwide distribution (two black and white copies).

(Continued)

*Primary Examiner* — Lyle Alexander
(74) *Attorney, Agent, or Firm* — Suzannah K. Sundby, Esq.; Smith, Gambrell & Russell, LLP

(57) ABSTRACT

A rapid diagnostic device, assay and multifunctional buffer reagent are provided for the detection of a target analyte in a fluid test sample. The 2-step assay utilizes a dual component flow-through device comprising a test unit and a dried indicator reagent delivery unit for receiving the fluid sample and multifunctional buffer, respectively. The test unit comprises a reaction zone containing immobilized capture reagent that can bind to the target analyte, an absorbent zone supporting the reaction zone, and optionally, a blood separation zone in lateral fluid communication with the reaction zone. The delivery unit comprises a label zone permeated with a dried indicator reagent which can be placed in transient fluid communication with the reaction zone of the test unit during the assay procedure. The rapid diagnostic assay system reduces the number of assay reagents, method steps and time required for performance compared to other conventional assays.

21 Claims, 6 Drawing Sheets

(56) References Cited

U.S. PATENT DOCUMENTS

| | | | |
|---|---|---|---|
| 4,517,288 | A | 5/1985 | Giegel et al. |
| 4,632,901 | A | 12/1986 | Valkirs et al. |
| 4,826,759 | A | 5/1989 | Guire et al. |
| 4,912,034 | A | 3/1990 | Kaira et al. |
| 4,916,056 | A | 4/1990 | Brown, III et al. |
| 4,943,522 | A | 7/1990 | Eisinger et al. |
| 4,960,691 | A | 10/1990 | Gordon et al. |
| 5,008,080 | A | 4/1991 | Brown, III et al. |
| 5,149,622 | A | 9/1992 | Brown et al. |
| 5,160,701 | A | 11/1992 | Brown, III et al. |
| 5,185,264 | A | 2/1993 | Makela |
| 5,459,078 | A | 10/1995 | Kline et al. |
| 5,670,381 | A | 9/1997 | Jou et al. |
| 5,726,013 | A | 3/1998 | Clark |
| 5,763,262 | A | 6/1998 | Wong et al. |
| 5,877,028 | A | 3/1999 | Chandler et al. |
| 5,879,951 | A | 3/1999 | Sy |
| 6,057,165 | A | 5/2000 | Mansour |
| 6,087,184 | A | 7/2000 | Magginetti et al. |
| 7,531,362 | B2 * | 5/2009 | Chan ............... 436/164 |

OTHER PUBLICATIONS

Original of MedMira Laboratories Inc., HIV/HCV Combination Test Instructions, 2000, ad for worldwide distribution (two black and white copies).

Original of MedMira Laboratories Inc., Hep B Core Antibody and Hep B Surface Antigen—Instruction on Whole Blood, 2000, ad for worldwide distribution (two black and white copies).

Original of MedMira Laboratories Inc., HIV-1/HIV-2 Whole Blood Test Instructions, 2000, instructions for test kit (two black and white copies).

Reconstruction of MedMira Laboratories Inc., MedMira Rapid HIV Test Kit Serum or Plasma Testing, 2000, ad for worldwide distribution (one color copy and one black and white copy).

Reconstruction of MedMira Laboratories Inc., HIV/HCV Combination Test Instructions, 2000, ad for worldwide distribution (one color copy and one black and white copy).

Reconstruction of MedMira Laboratories Inc., Hep B Core Antibody and Hep B Surface Antigen—Instruction on Whole Blood, 2000, ad for worldwide distribution (now retitled as "Hep B Core Antibody and Hep B Surface" (one color copy and one black and white copy).

Reconstruction of MedMira Laboratories Inc., HIV-1/HIV-2 Whole Blood Test Instructions, 2000, instructions for test kit (one color copy and one black and white copy).

Serum or Plasma Testing; MedMira Laboratories., Mississauga, Ontario, Canada L4W 4T6; 3 Minute Antigen Sensitized Membrane Immunoassay for Direct Detection of HIV 1 & 2 Antibodies.

International Preliminary Examination Report in corresponding International Application No. PCT/CA02/01210; Date of Report: Oct. 1, 2003.

PCT Written Opinion in corresponding International Application No. PCT/CA02/01210; Mailing Date: Jul. 15, 2003.

First Official Action in corresponding Chinese Application No. 02819646.5; Date of Dispatch: Oct. 21, 2005.

First Official Action in corresponding European Patent Application No. 02 753 996.4-2404, dated Oct. 7, 2005.

* cited by examiner

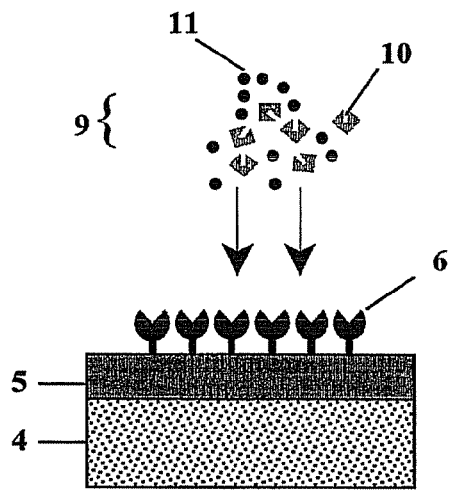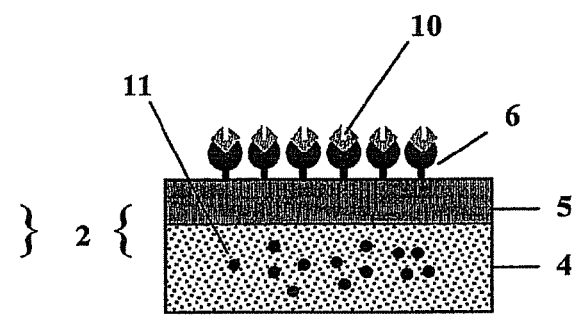
Fig. 2A Fig. 2B
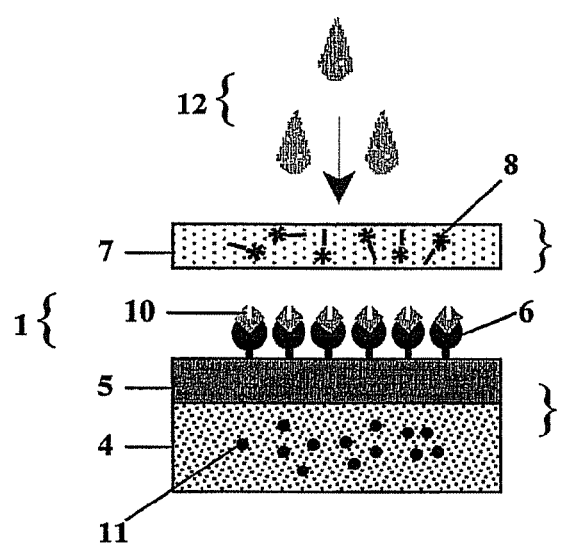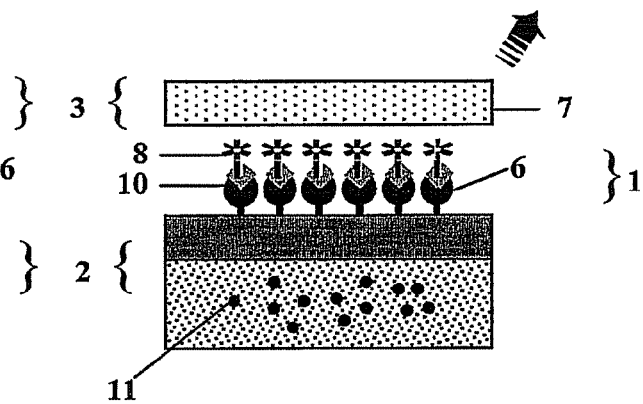
Fig. 2C Fig. 2D

RAPID DIAGNOSTIC DEVICE, ASSAY AND MULTIFUNCTIONAL BUFFER

CROSS-REFERENCE TO RELATED APPLICATIONS

This application is a continuation of Ser. No. 13/243,293, filed Sep. 23, 2011, now U.S. Pat. No. 8,287,817 which is a divisional of Ser. No. 12/285,868, filed Oct. 15, 2008, now U.S. Pat. No. 8,025,850, which is a continuation of application Ser. No. 10/163,675, filed Jun. 6, 2002, now U.S. Pat. No. 7,531,362, which claims the benefit of Provisional Application Nos. 60/296,147 and 60/309,477, filed Jun. 7, 2001 and Aug. 3, 2001, respectively, the entire contents of each of which are hereby incorporated by reference in this application.

FIELD OF THE INVENTION

An improved rapid diagnostic device, assay and multifunctional buffer are provided for the detection of a target analyte in a fluid test sample. The assay utilizes a multifunctional buffer reagent and flow-through device comprising a test unit in combination with a detachable dried indicator reagent delivery unit. A method for utilizing the flow-through device, a test kit and a formulation for generating the multifunctional buffer are also provided.

BACKGROUND OF THE INVENTION

Diagnostic assays have become an indispensable aid in medical and research fields for detecting a variety of components in biological fluids and tissue samples such as drugs, hormones, enzymes, proteins, antibodies, and infectious agents. A fundamental principle underlying the operation of a number of these assays is a specific recognition and binding reaction that occurs between two or more members to form a complex that can subsequently be detected. Normally, the members involve a capture reagent (e.g. receptor) that will specifically recognize and bind to a target analyte of interest (e.g. ligand) in a fluid test sample (e.g. whole blood, plasma, serum, urine, saliva, etc.). Moreover, a visually detectable indicator reagent is included in the reaction which will recognize and bind to any analyte complexed with the capture reagent to produce a signal indicating that a positive reaction has occurred. In particular, immunological assays are designed to function on the basis of antibody recognition and selective binding reaction to antigen and accordingly, have proven extremely valuable over the years in clinical applications for the detection of numerous infectious disease states.

In order to achieve accurate results, however, immunoassays often require precision in performing a series of time-consuming steps, as well as technical knowledge in operating sophisticated laboratory equipment. Accordingly, their use in diagnosing infectious disease has been essentially confined to clinical facilities that have the necessary resources for making such determinations including highly trained technical personnel and laboratories equipped with appropriate diagnostic equipment.

On this basis, as with many technologies, immunodiagnostic testing is evolving towards more simplistic approaches in the rapid identification and diagnosis of infectious disease states. The need for a simplistic qualitative assay for detecting analyte in a biological sample is becoming more desirable since it would offer an appealing possibility for use in less conventional settings having limited resources, e.g. physician's office, or domestic household. Whether in a public health clinic or a rural setting, it is preferable that an assay for detection of a target analyte in a fluid test sample be performed without the aid of complicated instruments and the requisite skills and knowledge of professionally trained personnel.

Another important factor to consider in pursuit of improved diagnostic testing is the lack of, or limited availability of, freezers and refrigeration in many third world countries. On this basis, it has become more desirable to develop assay reagents that will maintain their stability and integrity at room temperature for prolonged periods of time. Presently, some diagnostic devices and methods require the use of several assay reagents which have varying stability depending on the temperature at which they are stored and handled. Some of these reagents are stable at room temperature and may be stored for short periods of time, while others are relatively unstable and begin to deteriorate quickly, thereby adversely affecting the overall sensitivity and reliability of the assay. Thus, most commercially available diagnostic devices require at least one or more of the necessary reagents be kept at low temperatures in order to ensure their stability. Accordingly, a diagnostic device incorporating reagents that can be stored at ambient temperatures and remain stable for long periods of time while retaining all, or most, of its initial activity would have a clear advantage over current state of the art devices. On this basis, a factor worth considering towards simplifying diagnostic testing and thus, making it more practical and widely operational, is to minimize the number of assay reagents (e.g. mixing, washing, diluting solvents, etc.) and integrated steps in the assay protocol.

An immunodiagnostic assay which is simple to use, rapid and reliable would also be advantageous in improving screening and diagnostic services. According to the U.S. Center for Disease Control and Prevention report, rapid diagnostic tests enable healthcare providers to supply within minutes the test results to patients at the time of testing, thus potentially increasing the overall effectiveness of counseling and testing programs. It would also be expected that simplification of diagnostic devices and assays would likely be less costly to manufacture and perform compared to other conventional devices, thus making them economically feasible and more affordable to use in the interim. This is particularly desirable in third world countries where a simple, rapid, sensitive, and economical diagnostic device and assay would be ideal.

Towards this end, numerous analytical devices in an wide assortment of shapes, configurations and formats have been developed for detecting the presence of a target analyte in a fluid test sample, including chromatographic test strips, dipsticks, lateral flow and flow-through systems, to name a few. Many of these devices employ reaction membranes onto which a capture reagent capable of recognizing and binding to the target analyte is immobilized. In essence, the method of performing the assay typically involves applying a fluid test sample suspected of containing the target analyte, either directly or indirectly by filtration, to the reaction membrane. If the target analyte is present in the sample, it will bind to the capture reagent. Subsequent methods are then employed to determine whether the target analyte has bound to the capture reagent, thus indicating its presence in the sample.

U.S. Pat. No. 4,517,288 (Giegel, et al.) discloses methods for conducting ligand-binding assays using inert porous materials. In particular, the patent discloses immobilizing an immunological binding material (e.g. antibody) specific for the ligand of interest (e.g. antigen) within a finite test zone of the porous material and applying the ligand to the test zone, which will be captured by the immobilized binding material.

Immobilization of the binding material to the porous material may be achieved by any number of conventional methods including adsorption, covalent bonding, use of a coupling agent, etc. An enzyme-labeled indicator reagent, which will also recognize and bind with the ligand, is then applied to the test zone where it will become immobilized in an amount directly proportional to that of ligand present in the zone. A solvent is then applied to the center of the test zone to remove any unbound indicator reagent, thus enabling the determination of a signal to be made, with or without the aid of appropriate analytical instruments.

A more sophisticated version of a specific binding assay is described in U.S. Pat. Nos. 4,094,647, 4,235,601 and 4,361,537 (Deutsch, et al.), which incorporates a chromatographic test strip capable of transporting a developing liquid by capillary action. The test strip is designed so that it has a first zone for receiving a sample, a second zone impregnated with a first reagent capable of being transported by the developing liquid and a third zone impregnated with a third reagent. In addition, the device comprises a measuring zone and a retarding element which may be either the second reagent or the material of the strip. The first reagent is capable of reacting with one of the group consisting of (1) the sample, (2) the sample and the second reagent, or (3) the second reagent in competition with the sample, to form a product in an amount dependent on the characteristic being determined. A sample is contacted with the first zone and the strip is then dipped into the developing liquid to bring about transport of the sample and the first reagent to form the reaction product. The retarding element slows transport of either the product or the first reagent (the moving reagent) to spatially separate the two and the amount of the moving element is then measured at the measurement location.

A variation of the device by Deutsch, et al. is described in U.S. Pat. No. 4,960,691 (Gordon et al.) for the analysis of antigens, antibodies or polynucleotides, which also uses a length of a chromatographic material (i.e. test strip), a solvent carrier and mobile reagents. Essentially, the strip has three separate zones comprising a first zone impregnated with a mobile reagent reactive with the analyte of interest, a second zone for receiving a test sample suspected of containing the analyte, and a third zone impregnated with an immobilized reagent which selectively binds to the analyte, thereby rendering the analyte in an immobilized form. Each zone is sequentially located an equidistant from its neighbour along a longitudinal axis of the test strip. The device optionally comprises fourth and fifth zones impregnated with indicator reagents that will provide a means of detecting the presence of the analyte. The method involves depositing the test sample in the second zone, followed by solvent addition to the strip at the end where the first zone is located so that sequential movement and arrival of the analyte and first reagent eventually occurs at the third zone. The site relationship between the second and third zones is such that the analyte is immobilized against solvent transport at the third zone prior to the first reagent reaching the third zone. Any interfering non-analyte sample components, which are reactive with the first reagent, are cleared from the third zone by solvent transport prior to the arrival of the first reagent to the third zone. Multiple and single pathway devices are also disclosed for accomplishing a variety of multi-step assay procedures.

U.S. Pat. No. 4,168,146 (Grubb, et al.) discloses the use of test strips for carrying out sandwich-type immunoassays. The strips are formed of bibulous carrier materials to which antibodies have been attached by adsorption, absorption or covalent bonding. Preferred test strip materials include cellulose fibre-containing materials such as filter paper, ion exchange paper and chromatographic paper. Also disclosed are uses of materials such as cellulose thin-layer chromatography discs, cellulose acetate discs, starch and three-dimensional cross-linked materials such as Sephadex (Pharmacia Fine Chemicals, Uppsala Sweden). The immunoassay is performed by wetting the test strip with a measured volume of a test sample suspected of containing the antigen. Any antigen present in the test sample migrates by capillary action along the test strip. However, the extent of migration of the antigen over a fixed time period is determined by the antigen concentration in the test sample because the bound antibodies retard the migration of the antigens for which they are specific. Afterwards, the antigen-containing areas of the diagnostic device are indicated by the addition of labeled antibodies.

An immunodiagnostic flow-through system comprising a series of method steps is disclosed in U.S. Pat. No. 4,632,901 (Valkirs, et al.). The first step involves taking a fluid test sample suspected of containing a first member of a specific binding pair (e.g. antigen) and pouring it onto a porous material to which a second member of the specific binding pair (e.g. antibody) is immobilized. Influenced by the capillary action properties of an absorbent material, the fluid test sample is drawn downwards in a vertical direction through the porous material and pass the immobilized antibody. Any antigen present in the sample will subsequently be captured by the immobilized antibody. The second step involves passing a separate solution of labeled antibody through the porous material so that the labeled antibody may bind to the antigen already captured by the immobilized antibody to form a three-membered complex. Any unreacted or unbound labeled antibody is then flushed away from the porous material via a third step, normally referred to as a washing step, using a suitable reagent which may then be followed by an incubation period. Finally, a fourth step involving a separate solution containing a substrate reactive with the label on the antibody of the second solution is added to cause a visible color change indicative of the presence of the antigen of interest. To facilitate accurate performance of this method, the apparatus is designed in such a way as to funnel the sample through to the absorbent material which, by capillary action, draws the sample through the material and into the bottom of the apparatus.

An immunodiagnostic flow-through system described by Liotta in U.S. Pat. No. 4,446,232 utilizes a combination of two different reaction zones arranged in three separate layers. The first reaction zone comprises two layers fabricated from porous material wherein the first and second layers are impregnated with soluble enzyme-linked antibody and immobilized antigen, respectively. The third layer, or second reaction zone, contains immobilized indicator reagent that will react with the enzyme linked to the antibody of the first reaction zone to produce a color. If a liquid sample contains the antigen of interest, then after the sample is applied to the first reaction zone, the antigen contained therein will bind with the soluble enzyme-linked antibody and diffuse through to the second reaction zone following a short incubation period. The presence of antigen will be detected when the enzyme reacts with the indicator reagent to produce a color. By contrast, if a liquid sample does not contain any antigen, then the enzyme-linked antibody will migrate to the second layer of the first reaction zone, aided by diffusion of the fluid test sample, where it will bind to immobilized antigen. The binding reaction that occurs will prevent any enzyme-linked antibody from reaching the second reaction zone where it would react with the indicator reagent. Thus, in this particular scenario, no color is observed indicating the lack of antigen in the fluid test sample.

While the methods and devices described above may provide compact and somewhat reliable means for performing immunodiagnostic assays, several problems regarding their use still exist. In particular, one of the disadvantages encountered in determining the presence or absence of a target analyte in the majority of cases is the requirement to perform several addition and washing steps using a range of solvents. The washing steps are essential at various stages of the assay protocol in order to prevent undesired cross-reactions and to remove any excess unbound reagents and substances which may subsequently interfere with the results. Unfortunately, this only complicates the overall procedure and effectively reduces the level of efficiency desired in order to develop an improved and simplified version of an immunodiagnostic assay. Thus, the need to adhere to several addition, washing and incubation steps has largely limited these procedures to clinical settings where skilled personnel and sophisticated equipment are available to carefully monitor and perform the assay with precision and accuracy.

In addition, immunodiagnostic assays that employ chromatographic test strips or dipsticks suffer from a problem regarding sequential treatment with one or more solvents at various stages of the assay procedure. As each solution is added to the device, or as each device immersed into successive solutions, the opportunity for spillage or contact between the solutions and the user are enhanced, thus leading to possible contamination and reduction in the reliability of the test.

Depending on the assay and device used, it is usually necessary that the test sample be diluted with an appropriate reagent prior to application so that it will diffuse more easily throughout the porous material and/or not overwhelm the concentration of the labeled reagent. However, dilution of the test sample not only reduces the speed and ease of performing an assay by including an additional step and reagent, but it can also reduce the sensitivity of an assay due to the correlation of analyte concentration to the detection signal generated.

A further disadvantage associated with the use of some immunodiagnostic devices, particularly those incorporating lateral-flow techniques, is that they characteristically require long incubation periods at various stages of the procedure. Depending on the relative mobility of the analyte of interest, the type of reagents and solvent used, and the site relationship between the different reaction zones, adequate time is essential in order to allow for efficient migration of all the various components along the chromatographic solid phase material. Moreover, the lateral flow technique often contributes to a higher incidence of inaccurate results due to the tendency of mobile reagents to accumulate at, rather than clear, the periphery of the reaction zone. As a result, these reagents will often interact at the zone and produce color products that may be easily mistaken for a true positive or negative result.

Accordingly, the present invention provides an improved rapid diagnostic device, assay and multifunctional buffer for the detection of a target analyte in a fluid test sample which is efficient, reliable and practical to perform. The simplified 2-step assay utilizes a multifunctional buffer reagent and a dual component flow-through device comprising a test unit in combination with a detachable dried indicator reagent delivery unit which are capable of receiving the fluid test sample and multifunctional buffer, respectively.

The multifunctional buffer serves as a combination washing, diluting, wetting and resolubilizing reagent, without sacrificing the sensitivity or specificity of the diagnostic assay. Additionally, the buffer is formulated to preserve and optimize protein stability, as well as minimize, if not eliminate, non-specific interactions that might lead to the generation of a false signal.

SUMMARY OF THE INVENTION

An object of the present invention is to overcome the disadvantages associated with existing rapid diagnostic assays by providing an improved device, method and multifunctional buffer reagent.

Using the simplified device and single buffer reagent of the present invention, a qualitative and semi-quantitative assay (1) can be performed and read easily, (2) requires a minimum number of steps, (3) does not require lengthy incubation periods, and (4) is highly sensitive, specific and reliable. Typically, as little as a single drop (50 µL) of a fluid test sample is needed to perform the assay. Moreover, the device and assay of the present invention is particularly advantageous in that it is not only convenient and simple to use, but the device and reagents can be stored at room temperature for long periods of time without diminishing the activity or sensitivity of the assay.

The combination of features associated with the present invention relates to the implementation of a flow-through technique in conducting diagnostic assays that are based on specific binding reactions between two or more complementary members. On this basis, the rapid diagnostic device, assay and multifunctional buffer of the present invention have broad applicability in a variety of specific binding pair assay methods that essentially employ a capture reagent which will recognize and bind to a target analyte of interest. For example, the device of this invention can be used in an immunodiagnostic assay for the detection of either antigen or antibody in a fluid test sample and is adaptable for use in a sandwich or competitive detection format.

The kinetics of the reaction between the target analyte and the indicator reagent are extremely rapid and complete because the assay device and procedure operates on the basis of a flow-through format. Moreover, the method of the present invention improves the accuracy of the assay compared to conventional assays since the final step of the assay involves the addition of resolubilized indicator reagent to the target analyte after the analyte has already complexed with the capture reagent. By contrast, most conventional assays require premixing of the indicator reagent with a fluid test sample before addition to the capture reagent. As a result, the overall sensitivity of the assay is reduced due to the likelihood of the indicator reagent coming into contact with contaminants present in the test sample during the initial stage of the assay protocol, instead of only the analyte of interest.

The improved rapid diagnostic device is advantageously used in combination with a multifunctional buffer reagent for the purpose of detecting a target analyte in a fluid test sample based on the principle of a specific binding interaction between two or more complementary members. The device of the invention comprises, as a first component, a test unit capable of receiving a fluid test sample, in combination with a second component, namely a dried indicator reagent delivery unit, capable of receiving the multifunctional buffer. The test unit comprises (1) a reaction zone containing immobilized capture reagent that can specifically recognize and bind to the target analyte, (2) an absorbent zone supporting the reaction zone, and optionally, (3) a blood separation zone in lateral fluid communication with the reaction zone. The dried indicator reagent delivery unit comprises a label zone permeated with a dried indicator reagent which is resolubilized upon addition of the multifunctional buffer. The reaction zone of the test unit is oriented so that the label zone of the dried indicator reagent delivery unit can be brought into fluid communication therewith after the fluid test sample is applied to the test unit.

In the case of an immunodiagnostic assay, for example, in which the analyte of interest is an antigen, an antibody, preferably a monoclonal antibody or an affinity purified polyclonal antibody for the antigen, is bound to the reaction zone as the capture reagent. In a preferred embodiment, the reaction zone is comprised of a porous membrane compatible for immobilization of the capture reagent and has low non-specific binding for the indicator reagent. Any non-specific binding sites on the surface of the porous reaction membrane are inactivated by applying a protein blocking agent. The specificity and affinity of the immobilized capture reagent is such that it efficiently binds and concentrates any analyte contained in the fluid test sample within a defined region as the sample diffuses by capillary action from the reaction membrane to the absorbent zone directly underneath.

The sensitivity of reaction-membrane type immunoassays (i.e. the ability to detect very low levels of target analyte) can be increased if the sample is concentrated through the reaction membrane. Therefore, concentration of analyte on the reaction membrane is achieved by having an absorbent material, defining the absorbent zone, placed directly beneath the reaction membrane that will draw the fluid test sample in, leaving only captured analyte on the upper surface of the reaction membrane. Since the absorbent material is in fluid communication with the reaction membrane, the material is selected on the basis of having physical properties (e.g. pore size, wicking power, etc.) which will effectively induce the flow of fluid through the reaction membrane, adequately hold assay sample and reagent fluids, and provide support for the membrane.

To facilitate the detection of a target analyte in a whole blood sample, an alternate embodiment of the present invention provides a test unit capable of receiving and separating the fluid portion of a whole blood sample from the red blood cells (RBC), while transporting the RBC-free fluid portion of the sample to the reaction zone for the detection of analyte. This particular feature is useful in preventing any interference during visualization of a colour reaction for the detection of analyte (i.e. the use of "direct" labels which provide a visually detectable signal directly without the aid of instruments) and also avoids the necessity to obtain a preliminary extraction of serum or plasma in settings where proper equipment to perform such a procedure is unavailable.

Thus, in the case where the fluid test sample to be analyzed is a whole blood sample, the test unit optionally features a separate blood separation zone in lateral fluid communication with the reaction zone. In general, the blood separation zone functions to selectively retain cellular components (i.e. red blood cells) contained within the whole blood sample and deliver the remaining components of the blood sample, including any analyte, to the reaction zone. A first end of the blood separation zone, located a short lateral distance from the reaction zone, defines a region for receiving the whole blood sample prior to introduction of the analyte at the reaction zone. A second end of the blood separation zone is contiguous with, and thus in direct fluid communication with, the reaction zone thereby promoting the capillary movement of the RBC-free fluid portion of the blood sample from the first end to the reaction zone for direct analysis of the target analyte. Thus, in effect, the blood separation material functions as a lateral flow material for the selective removal of an effective amount of red blood cells from the whole blood sample to prevent interference with the visual detection of the analyte, while allowing other components of the sample to flow with relatively unimpaired movement through the test unit.

In a preferred embodiment, the blood separation zone is an elongate or rectangular strip of porous material employing a hydrophobic carrier or backing and having intrinsic properties which enable it to preferentially entrap or retain the red blood cells in the sample within the blood separation zone. The carrier or backing provides support for the blood separation material and reduces seepage of the whole blood sample as the RBC-free fluid portion migrates along the material towards the reaction zone.

The second component of the device, namely the dried indicator reagent delivery unit, comprises a label zone permeated with a dried indicator reagent. The label zone of the dried indicator reagent delivery unit is capable of being placed in transient fluid communication with the reaction zone of the test unit shortly following application of the fluid test sample to the test unit.

Impregnating the label zone of the dried indicator reagent delivery unit with a permanently detectable indicator reagent eliminates the need to perform separate resolubilization steps involving precise measuring, adding and premixing with a suitable solvent which increases the possibility of user error. In a preferred embodiment, the label zone comprises a filter medium selected on the basis of having a pore size large enough so that when the dried indicator reagent is resolubilized by addition of the multifunctional buffer, it will easily flow through an exposed area of the porous filter medium by the process of diffusion. The shape and dimensions of the dried indicator reagent delivery unit are such that it will hold and effectively channel the multifunctional buffer through the porous filter medium when the label zone is placed in transient fluid communication with the reaction zone of the test unit during the assay procedure.

According to another important aspect of the invention, methods and devices are provided utilizing "direct" labeled specific binding materials (i.e. colloidal particle labeled materials) which are dried onto a filter medium and hence, are capable of being rapidly resolubilized and transported to the reaction zone in the presence of the multifunctional buffer. Direct labels are well known in the art and highly advantageous for their use in rapid diagnostic systems. Direct labels are capable of producing a visually detectable signal without the aid of instrumentation or the addition of ancillary reagents and are stable when stored in the dry state. Supplying the indicator reagent by way of incorporating it within the filter medium in a dried form provides an inexpensive and convenient means of storing such reagent. The preferred label for carrying out diagnostic assays is colloidal metal particles, more preferably colloidal gold, although other direct labels may be employed which include, but are not limited to, non-metal sols, dye sols, latex particles, carbon sol, and liposome contained colored bodies.

According to a further important aspect of the present invention, there is provided an aqueous composition suitable for use as a multifunctional reagent in a diagnostic assay, comprising: (1) a biological buffer to maintain the pH between about 7.0 to 10.0; (2) at least one surfactant to reduce non-specific binding of assay reagents while simultaneously avoiding inhibition of a specific binding interaction; (3) a high molecular weight polymer as a dispersing and suspending reagent having a molecular weight in a range of from about $2 \times 10^2$ to about $2 \times 10^6$ D; (4) a pH stabilizer to maintain the pH of the multifunctional buffer between about pH 7.0 to 10.0; (5) an ionic salt to reduce the non-specific binding of antibodies; (6) at least one preservative to reduce bacterial and microbial growth; and (7) a calcium chelator to prevent a whole blood test sample from clotting; wherein the biological buffer, surfactant, high molecular weight polymer, pH stabilizer, ionic salt, preservative and calcium chelator are all at effective concentrations.

The improved buffer formulation does not require ancillary additives or the maintenance and inspection by laboratory instruments. More importantly, however, is the multifunctional nature of the buffer reagent which enables it to serve as a combination wash solution, diluent, resolubilization and solvent transport reagent, thereby eliminating the need for several separate solutions and steps to be performed during the assay protocol. The development of a single multifunctional buffer greatly simplifies the assay procedure by reducing the time and manual steps required to perform the assay, thereby minimizing the likelihood for user error. In addition, utilizing the multifunctional buffer in a flow-through format promotes quick release and enhanced mass transfer of the dried indicator reagent from the dried indicator reagent delivery unit to the test unit immediately following resolubilization. Other functional properties exhibited by the multifunctional buffer are that it maintains protein stability, thereby preserving and optimizing the specific binding reaction that occurs between complementary binding members, i.e. capture reagent and target analyte. Moreover, upon resolubilization of the dried indicator reagent, the buffer helps to maximize signal generation in the case of a specific binding reaction and minimize nonspecific binding to the reaction membrane that might otherwise lead to the generation of a false signal.

According to yet a further aspect of the present invention, there is provided a simple 2-step procedure for performing a diagnostic assay comprising (1) depositing a fluid test sample onto the reaction zone of the test unit, or if a whole blood sample, onto a first end of a blood separation zone and shortly thereafter, bringing the test unit and the dried indicator reagent delivery unit into operable association therewith such that the label zone of the dried indicator reagent delivery unit is in transient fluid communication with the reaction zone of the test unit, and (2) adding the multifunctional buffer to the dried indicator reagent delivery unit followed by removal of the dried indicator reagent delivery unit to observe the test result. Following addition of the multifunctional buffer to the dried indicator reagent delivery unit, the buffer reagent diffuses through the label zone to reconstitute the indicator reagent and transport it to the reaction zone where it will bind with any captured analyte. If analyte is present in the fluid test sample, a detectable signal will appear in the reaction zone which can be visually inspected for color and thus, a determination of the presence or absence of analyte made following removal of the dried indicator reagent delivery unit. An important advantage provided by the present invention is that the binding affinity of the capture reagent is capable of immobilizing and optimizing exposure of the analyte in the flowing stream of reconstituted indicator reagent so that it is accumulated in the reaction zone and thus, efficiently separated from the background stream of non-concentrated indicator reagent.

The present invention also provides a diagnostic test kit for use in the detection of a target analyte in a fluid test sample suspected of containing the analyte. Essentially, the kit comprises in a packaged combination: (1) the rapid diagnostic assay device comprising both the test unit and dried indicator reagent delivery unit as described above; (2) a multifunctional buffer reagent for reconstitution of the dried indicator reagent; and (3) instructions for performing the diagnostic assay. The test kit preferably includes a suitable container for housing the test unit and the dried indicator reagent delivery unit in order to safeguard the solid phase materials and dried indicator reagent from contamination, as well as to provide ease and convenience in handling of the assay device. Optionally, the test kit also includes a means for applying the test sample and multifunctional buffer to the test unit and dried indicator reagent delivery unit, respectively (e.g. disposable pipettes).

BRIEF DESCRIPTION OF THE DRAWINGS

FIG. 2A is a diagrammatic illustration of a test sample applied to the reaction zone of the test unit which contains target analyte;

FIG. 2B is a diagrammatic illustration of target analyte complexed with the capture reagent after the test sample has completely diffused through the reaction zone and into the absorbent zone of the test unit;

FIG. 2C is a diagrammatic illustration of the dried indicator reagent delivery unit in fluid communication with the reaction zone of the test unit, to which the multifunctional buffer is added;

FIG. 2D is a diagrammatic illustration of resolubilized indicator reagent reacted with complexed capture reagent and analyte following addition of the multifunctional buffer to the dried indicator reagent delivery unit;

Figure 1A:
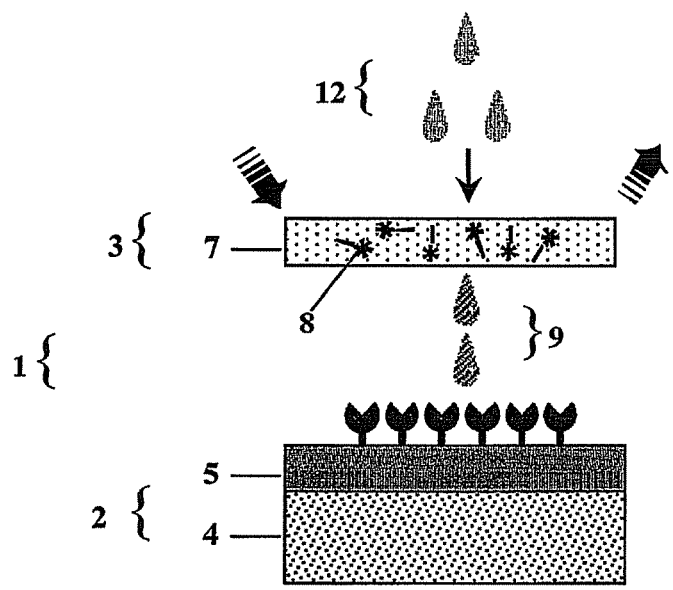
FIG. 1A is a diagrammatic illustration of a first embodiment of the flow-through diagnostic device of the present invention comprising the test unit and dried indicator reagent delivery unit.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

DETAILED DESCRIPTION OF THE INVENTION

Unless defined otherwise, all technical and scientific terms used herein have the same meaning as commonly understood by one of ordinary skill in the art to which this invention belongs. It must also be noted that, as used in the specification and the appended claims, the singular forms "a," "an" and "the" include plural referents unless the context clearly dictates otherwise. For example, reference to an "antigen" or "antibody" is intended to include a plurality of antigen molecules or antibodies.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

As employed throughout the disclosure, the following terms, unless otherwise indicated, shall be understood to have the following meanings:

Absorbent Zone—the term "absorbent zone" is intended to include one or more layers of a permeable (e.g. porous or fibrous) material, which layers can be the same or different, and are capable of drawing or wicking fluid by capillary action. The absorbent zone should also be capable of absorbing a substantial volume of fluid that is equivalent to or greater than the total volume capacity of the material itself, and thus have a high absorbent capacity.

Analyte (or target analyte)—the compound or composition of interest to be detected in a biologically derived fluid test sample. Examples of analytes may include drugs, hormones, polypeptides, proteins including immunoglobulins, polysaccharides, nucleic acids, and combinations thereof.

Antibody—an immunoglobulin, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

Antibodies useful in conducting the immunoassays of the present invention include those specifically reactive with various analytes the detection of which in biological fluids is desired. Such antibodies are preferably IgG or IgM antibodies or mixtures thereof, which are essentially free of association with antibodies capable of binding with non-analyte molecules. The antibodies may be polyclonal or monoclonal and are commercially available or may be obtained by mouse ascites, tissue culture or other techniques known to the art. A typical description of hybridoma procedure for the production of monoclonal antibodies may be found in Wands, J. R., and V. R. Zurawski, Gastroenterology 80:225 (1981); Marshak-Rothstein, A., et al.; J. Immunol. 122:2491 (1979); Oi, V. Y. and L. A. Herzenberg, "Immunoglobulin Producing Hybrid", Mishell B. B. and S. M. Shiigi (eds) Selected Methods in Cellular Immunology, San Francisco: W. H. Freeman Publishing, 1979; and U.S. Pat. No. 4,515,893 issued to Kung, et al. The use of mixtures of monoclonal antibodies of differing antigenic specificities or of monoclonal antibodies and polyclonal antibodies may be desired. It is further contemplated that fragments of antibody molecules may be used as specific binding reagents according to the invention including half antibody molecules and Fab, Fab' or F(ab')$_2$ fragments known in the art. Regardless of the particular source or type of antibodies, however, it is preferred that they be generally free of impurities. The antibodies may be purified by column chromatographic or other conventional means but are preferably purified according to known affinity purification techniques. Antibodies materials may also be labeled with colloidal particles according to the invention and used in sandwich type assays for the detection of antigen analytes or in competition assays for the detection of antibody analytes.

Antigen—antigens and haptens useful in carrying out the immunoassays of the present invention include those materials, whether natural or synthesized, which present antigenic determinants for which the analyte antibodies are specifically reactive when used according to the present invention. Synthesized antigens include those which are constructed according to conventional chemical syntheses as well as those constructed according to recombinant DNA techniques. Antigen materials may also be labeled with colloidal particles according to the invention and used in sandwich type assays for the detection of antibody analytes or in competition assays for the detection of antigen analytes.

Blood Separation Zone—The term "blood separation zone" is intended to include a porous and/or fibrous material which is capable of retaining red blood cells (RBC) from a whole blood sample allowing the RBC-free fluid, including any target analyte, to migrate in a lateral flow by way of capillary action.

Capilliary Action—as used herein, the term "capillary" includes a capillary or other channel or pathway which permits a liquid to traverse a porous, fibrous or absorbent material. The material in capillary communication with the reaction membrane of the test unit is selected on the basis of having intrinsic properties which enable it induce flow of a fluid, either vertically or laterally, without the use of external means.

Capture Reagent—any compound or composition capable of recognizing a particular spatial and/or chemical structure of an analyte. In the case of an analyte which is a specific immunoglobulin species, the capture reagent may be the specific protein or epitope recognized by the immunoglobulin. Other types of capture reagents include naturally occurring receptors, antibodies, antigens, enzymes, Fab fragments, lectins, nucleic acids, avidin, protein A, and the like.

Fluid test sample—the fluid test sample is assayed to form a detectible reaction product on the reaction membrane of the test unit. In preferred assay embodiments, the fluid test sample is biologically derived (e.g. whole blood, plasma, serum, urine, saliva, etc.) and is suspected to include as the target analyte, typically an antigen, antibody, or hapten capable of being bound by the capture reagent immobilized on the reaction membrane.

Indicator Reagent—a conjugate comprised of a specific binding member to the target analyte and a label conjugated to the specific binding member which is capable of being visually detected. Additionally, the indicator reagent can be comprised of a general marker protein, e.g. Protein A, Protein G, or anti-IgG conjugated to a label. For example, in an assay for detecting antibody as a target analyte, a preferred indicator reagent would be protein A labeled with colloidal gold. Other indicator reagents may also include a labeled anti-human antibody directed to the antibody of interest, e.g. goat anti-human IgG labeled with colloidal gold for the detection of human antibody in a fluid test sample.

Label—a label may be any molecule bound or conjugated to a specific binding member or general marker protein which can produce a signal. In the subject invention, the label is preferably a "direct" label which is capable of spontaneously producing a detectible signal without the addition of ancillary reagents and will be easily detected by visual means without the aid of instruments. The preferred embodiment of the invention uses colloidal gold particles as the label. Other suitable labels may include other types of colloidal metal particles, minute colored particles, such as dye sols, and coloured latex particles. Many such substances will be well known to those skilled in the art.

Label Zone—The term "label zone" is intended to include a porous material which is impregnated with a dried indicator reagent that can be readily resolubilized upon addition of a buffer reagent thereto.

Reaction Zone—the term "reaction zone" is intended to include a porous material to which the capture reagent and other molecules employed in the analytical assay are bound as well as additional porous supporting material, if any, that forms the lower surface of the reaction zone.

Specific Binding Member—this describes two or more complementary members of a specific binding interaction which have binding affinity for one another. The specific binding members may be naturally derived or synthetically produced. One member of the specific binding interaction has an area on its surface, or a cavity, which specifically binds to and is therefore complementary to a particular spatial and/or chemical structure of the other complementary member. Examples of types of specific binding pairs are antigen-antibody, biotin-avidin/streptavidin, hormone—hormone receptor, receptor-ligand, enzyme-substrate, and the like.

1.0 Introduction

The present invention provides an improved rapid diagnostic device, assay and a multifunctional buffer for the detection of a target analyte in a fluid test sample, such as a body fluid. The rapid diagnostic device is not only simple to use and economical to manufacture, but it is reliable enough to be utilized in sensitive analytical assays without requiring lengthy incubation periods, extra washing steps, or dilution of the sample. Since the assay may be varied according to the target analyte in question, the present invention is useful for a wide variety of biological assays. For instance, a fluid test sample (e.g. serum, plasma, whole blood, saliva, urine, etc.) may be quickly and accurately analyzed for antigen, antibodies, natural or synthetic steroids, hormones, and the like.

The rapid diagnostic device useful in the practice of the invention is a dual component flow-through system comprising a test unit and a dried indicator reagent delivery unit capable of receiving the fluid test sample and multifunctional buffer, respectively. The test unit comprises a reaction zone containing immobilized capture reagent that can specifically recognize and bind to the target analyte and an absorbent zone supporting the reaction zone. The reaction zone of the test unit is oriented so that the label zone of the dried indicator reagent delivery unit can be brought into transient fluid communication therewith shortly after the fluid test sample is applied to the reaction zone of the test unit. To facilitate the detection of a target analyte in a whole blood sample, an alternate embodiment of the present invention provides a test unit further comprising a blood separation zone in lateral fluid communication with the reaction zone, whereby a first end of the blood separation zone located a short lateral distance from the reaction zone defines a region for receiving the whole blood sample. A second end of the blood separation zone may overlap slightly with the reaction zone so as to ensure direct fluid communication therewith. The dried indicator reagent delivery unit comprises a label zone containing a dried indicator reagent and is capable of being placed in transient fluid communication with the reaction zone of the test unit during the assay procedure.

The assay protocol is a simple 2-step procedure involving (1) depositing a fluid test sample onto the reaction zone of the test unit, or if a whole blood sample, onto a first end of the blood separation zone and shortly thereafter, bringing the test unit and the dried indicator reagent delivery unit into operable association such that the label zone of the dried indicator reagent delivery unit is in transient fluid communication with the reaction zone of the test unit, and (2) adding the multifunctional buffer to the dried indicator reagent delivery unit and removing the dried indicator reagent delivery unit to observe the test result. The multifunctional buffer passively diffuses through the label zone of the dried indicator reagent delivery unit to resolubilize the indicator reagent and transport it to the reaction zone of the test unit where it will bind to the corresponding analyte complexed with the capture reagent. If analyte is present in the fluid test sample, a detectable signal will appear in the reaction zone which can be easily visualized following removal of the dried indicator reagent delivery unit from the test unit. An advantage provided by the methodology of the present invention is the enhanced sensitivity and reliability of the test. This is achieved by maximizing the opportunity for thorough capture of the analyte, even at low concentrations. Additionally, the implementation of assay steps which increase the likelihood of contamination of the sample and reagents is eliminated altogether by the assay of the present invention.

2.0 Specific Binding Reaction

The assay device of the present invention is used to qualitatively and semi-quantitatively detect the presence of a target analyte in a fluid test sample. Analytes suitable for detection in the assay device are essentially members of a specific binding interaction such that one of the members is able to recognize and bind, usually non-covalently, to a complementary, non-identical member so as to form a stable complex that can be easily be detected, either directly or indirectly. The members of the specific binding reaction may be referred to as a target analyte and a capture reagent and may include a wide variety of biologically derived substances that may participate in an immunological reaction, e.g. antigen-antibody, or a non-immunological reaction, e.g. avidin and biotin, cell surface receptor and an effector agent, DNA and RNA, and so forth. For a disclosure of specific binding members see U.S. Pat. No. 3,996,345 (Ullman, et al.).

As applied to binding assays, the assay device of the present invention can be designed to detect any number of target analytes, for which there is a specific binding partner. The analyte usually is a peptide, protein, carbohydrate, glycoprotein, steroid, or other organic or inorganic molecule for which a specific binding partner exists in a biological system, or can be synthesized. The binding assay essentially involves the specific binding of the analyte (i.e. the first specific binding member) to a capture reagent (i.e. the second specific binding member) immobilized on a solid phase material and additionally, an indicator reagent (comprising a label attached to an ancillary second specific binding member or a general marker protein). The immobilization of the capture reagent to the solid phase material forms a "capture situs" and thus, facilitates the separation or removal of the target analyte from other components of the test sample. The label, which enables the indicator reagent to produce a detectable signal signifying the presence of analyte in the fluid test sample, is achieved through direct or indirect binding of the binding member of the indicator reagent. Generally, the ancillary second specific binding member binds to the target analyte at a site which does not interfere with the specific binding interaction between the target analyte and the capture reagent. Exemplary, but not exclusive of the present invention, is the specific binding interaction that occurs as a result of antibody-antigen interactions.

It will be appreciated by those skilled in the art that while the rapid diagnostic assay device described herein is anticipated to be primarily employed in assaying either antigens or antibodies through the formation of an immune complex, that in fact, its applicability is considerably broader, and is not restricted to these molecules. At a minimum, the device merely requires that a first member that recognize and bind with a second member of a specific binding reaction. The first member can be conveniently termed a target analyte and the second member a capture reagent. While antigen and antibody are preferred embodiments of a target analyte and capture reagent, serving respective or alternative roles, the device can be used with a variety of capture reagent and analyte molecules. For example, hormone receptor molecules are a type of capture reagent molecule and can be attached to the reaction zone of the test unit and used to assay for the corresponding hormone analyte. Alternatively, a hormone could be bound to the reaction zone and used to assay for hormone receptors (Hermanson, G. T. (1996) Bioconjugate Techniques, Academic Press).

The system is also adaptable to the detection of DNA sequences. For example, a fluid test sample suspected of containing a DNA sequence as target analyte is deposited on the reaction zone and binds to a known complimentary DNA sequence immobilized as capture reagent on the reaction zone. Then, a labeled DNA probe is transported by way of the multifunctional buffer to the reaction zone. If hybridization occurs, the labeled DNA probe will be retained in a visually detectable form on the surface of the reaction zone. This system is described in Polsky-Cynkin, R., et al., Clin. Chem. 31/9, 1438 (1985).

Thus, it will be readily apparent to those skilled in the art that there are many such combinations of capture reagent-target analyte pairs that may be suitably employable in the present diagnostic device and method.

3.0 Assay Device and Methodology 3.1 Sandwich Technique

A preferred embodiment of the present invention employs a direct binding (sandwich) assay format. The format is based on the principle of a specific binding interaction that will occur between a target analyte comprising the first specific binding member, a capture reagent comprising a second specific binding member that is immobilized to a solid phase material, and a dried indicator reagent comprising an ancillary second specific binding member, or a general marker protein. The aforementioned members form a three-membered complex when the contents of a fluid test sample containing the target analyte are reacted with immobilized capture reagent, followed by the addition of the indicator reagent. In general, the diagnostic assay thus depends upon the ability of a second specific binding member to specifically recognize and bind to the first specific binding member. Depending upon the type of target analyte to be detected, an indicator reagent comprising an ancillary second specific binding member labeled with a visually detectable moiety is employed to determine the existence of such binding. The amount of indicator reagent detected and measured after the reaction can be correlated to the amount of analyte present in the test sample. For example, in the sandwich immunoassay format, a test sample containing an antigen, i.e. the target analyte, is contacted with a primary antibody which is immobilized on a solid phase material, i.e. the capture reagent. The solid phase material is subsequently treated with the indicator reagent, namely a secondary antibody that has been labeled with a visually detectable moiety. The secondary antibody then becomes bound to the corresponding antigen immobilized by the primary antibody immobilized to the solid phase material and any color change is then visually detected which is indicative of antigen present in the test sample.

Thus, in its simplest embodiment, FIG. 1A provides a diagrammatic illustration of the assay device 1 of the present invention which comprises two separate components, a test unit 2 and a dried indicator reagent delivery unit 3. The test unit 2 is comprised of a reaction zone 5 having its lower surface supported by an absorbent zone 4. The reaction zone 5 receives the fluid test sample 9 directly and provides clear visualization of a test result due to the presence of immobilized capture reagent 6 contained therein which is capable of recognizing and binding the target analyte of interest through a specific binding interaction. In a preferred embodiment, the reaction zone 5 is comprised of a porous membrane compatible for immobilization of the capture reagent 6 and has low non-specific binding for the indicator reagent 8. The absorbent zone 4 is preferably made from permeable material possessing intrinsic properties that enable it to draw fluid in by capillary action, adequately hold reagent and sample fluids, and additionally provide support for the reaction zone 5. The dried indicator reagent delivery unit 3 comprises a label zone 7 permeated with a dried indicator reagent 8. The dried indicator reagent 8 comprises a label and a specific binding member which will also recognize and bind to the analyte of interest, but at a site which does not interfere with the specific binding interaction between the target analyte and the capture reagent. The label zone 7 preferably comprises a filter medium selected on the basis of having a pore size large enough so that when the dried indicator reagent 8 is resolubilized by addition of the multifunctional buffer 12, it will easily flow through an exposed area of the label zone 7 by the process of diffusion. The shape and dimensions of the dried indicator reagent delivery unit 3 are such that it will hold and effectively channel the multifunctional buffer through the label zone 7 when placed in transient fluid communication with the reaction zone 5 of the test unit 2 during the final step of the assay procedure.

Figure 1B:
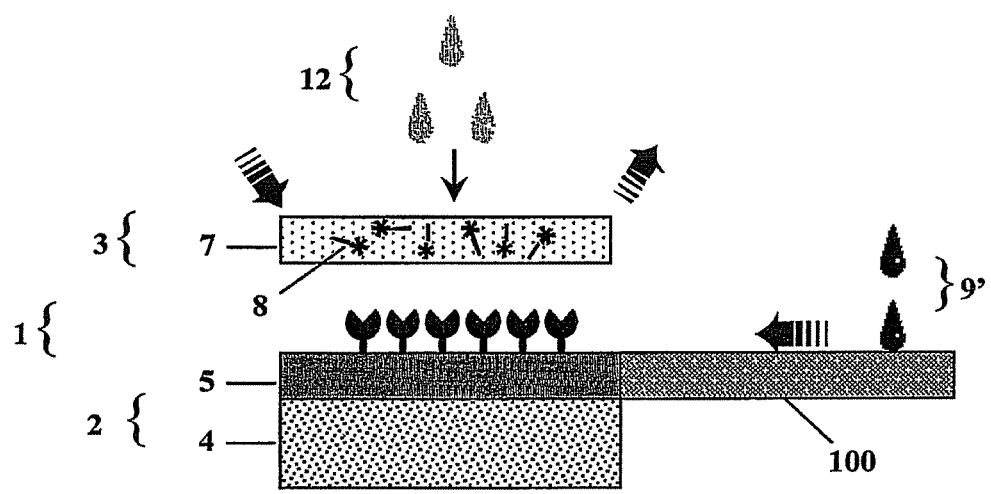
FIG. 1B is a diagrammatic illustration of a second embodiment of the flow-through diagnostic device of the present invention for analyzing a whole blood test sample comprising the test unit and dried indicator reagent delivery unit.

FIG. 1B provides a diagrammatic illustration of the assay device 1 of a second embodiment of the present invention which comprises two separate components, a test unit 2 and a dried indicator reagent delivery unit 3, wherein the test unit 2 additionally comprises a blood separation zone 100 capable of receiving and separating the fluid portion of a whole blood sample 9' from the red blood cells (RBC), while transporting a RBC-free fluid portion, including any analyte, to the reaction zone 5 for direct analysis. The preferred material for the blood separation zone 100 is selected on the basis of having intrinsic properties which enable it to preferentially entrap or retain the red blood cells in the sample 9' as the fluid portion migrates in a lateral direction towards the reaction zone 5.

FIG. 2 is a diagrammatic illustration showing the method of the invention using the device of FIG. 1A. In this particular instance, FIG. 2A shows a fluid test sample 9 containing the target analyte 10, as well as other non-essential components 11, which is applied to the reaction zone 5 of the test unit 2. As the fluid test sample 9 diffuses through the reaction zone 5 and into the absorbent zone 4 underneath, the free analyte 10 comes into contact with available sites of attachment on the capture reagent 6 and forms a complex, while unbound non-essential component 11 continues to be drawn into the absorbent zone 4 below (FIG. 2B). As shown in FIG. 2C, the label zone 7 of the dried indicator reagent delivery unit 3 is subsequently brought into fluid communication with the reaction zone 5 of the test unit 2 prior to the addition of the multifunctional buffer 12. Immediately following resolubilization of the dried indicator reagent 8 by the buffer 12, the indicator reagent 8 is transported to the reaction zone 5 of the test unit 2, where it will bind with any analyte 10 that has complexed with the capture reagent 6. The binding reaction of the indicator reagent 8 with the analyte 10 produces a visually detectable signal thereby indicating a positive result that is easily observed following removal of the dried indicator reagent delivery unit 3, as per FIG. 2D.

Figure 3A:
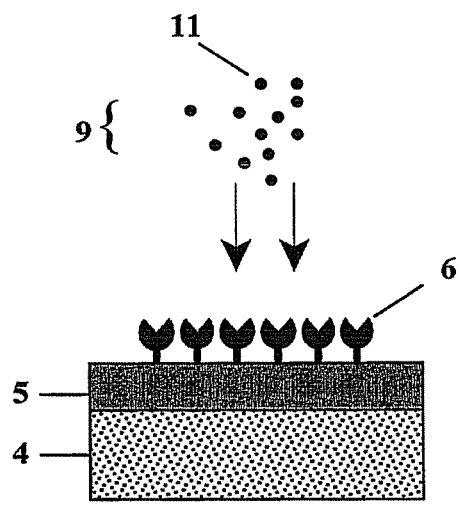
FIG. 3A is a diagrammatic illustration of a test sample applied to the porous reaction membrane of the test unit which does not contain target analyte.
Figure 3B:
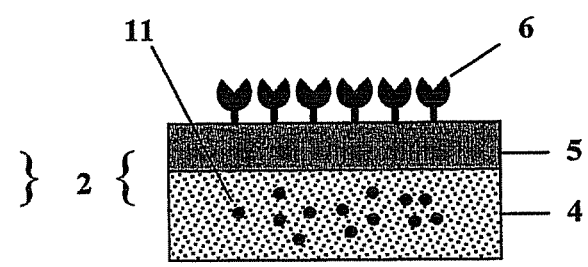
FIG. 3B is a diagrammatic illustration of uncomplexed capture reagent after the test sample has diffused through the reaction membrane and into the absorbent material of the test unit.
Figure 3C:
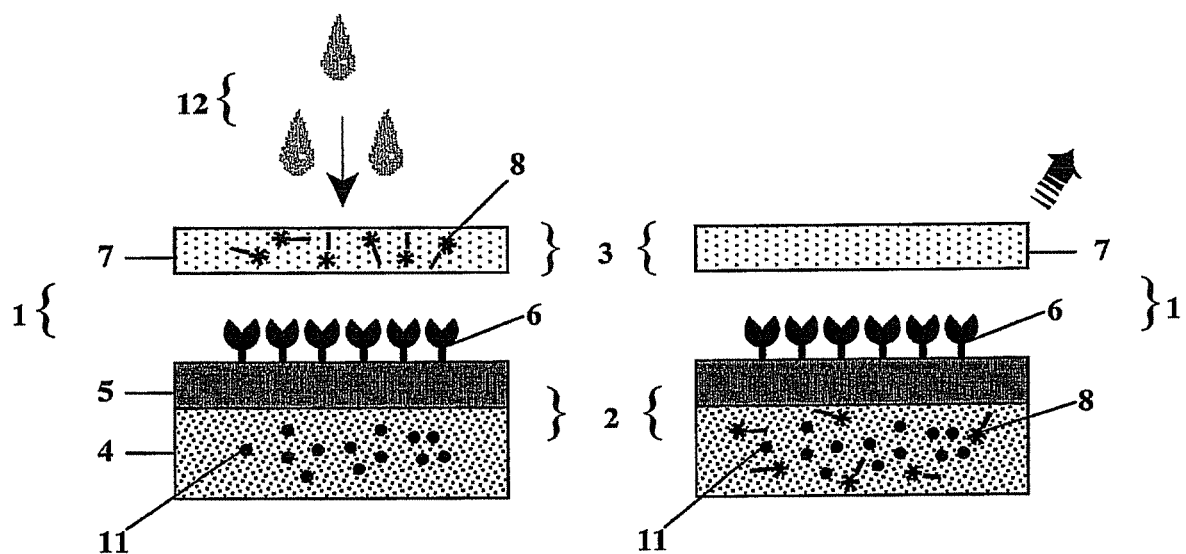
FIG. 3C is a diagrammatic illustration of the dried indicator reagent delivery unit in fluid communication with the reaction zone of the test unit, to which the multifunctional buffer is added.
Figure 3D:
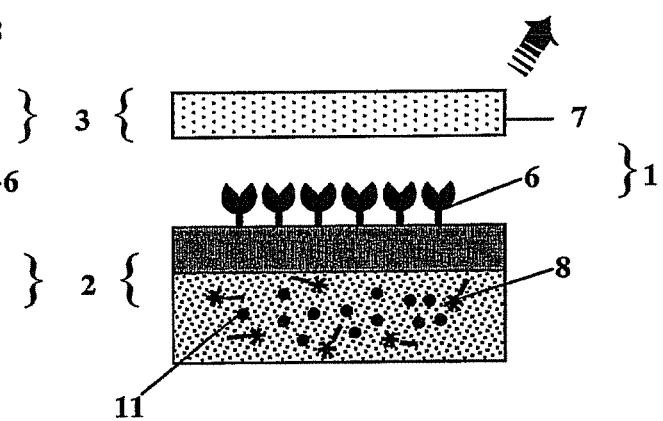
FIG. 3D is a diagrammatic illustration of unreacted indicator reagent following resolubilization by the multifunctional buffer after diffusing through the reaction zone and into the absorbent zone of the test unit.

FIG. 3A is a diagrammatic illustration showing the method of the invention using the device of FIG. 1A when a fluid test sample 9 devoid of target analyte is applied to the reaction zone 5 of the test unit 2. As the fluid test sample 9 diffuses through the reaction zone 5 and into the absorbent zone 4 underneath, the non-essential components 11 completely bypass the capture reagent 6, leaving the sites of attachment unoccupied (FIG. 3B). As shown in FIG. 3C, the label zone 7 of the dried indicator reagent delivery unit 3 is subsequently brought into fluid communication with the reaction zone 5 of the test unit 2 prior to the addition of the multifunctional buffer 12. Immediately following resolubilization of the dried indicator reagent 8 by the buffer 12, the indicator reagent 8 is transported to the test unit 2, where it diffuses through the reaction zone 5, pass the capture reagent 6 and into the absorbent zone 4 below due to the absence of any target analyte complexed with capture reagent 6. Following removal of the dried indicator reagent delivery unit 3, a color signal will not be detected thereby indicating a negative result due to the absence of binding between the indicator reagent 8 and complexed analyte.

Figure 6:
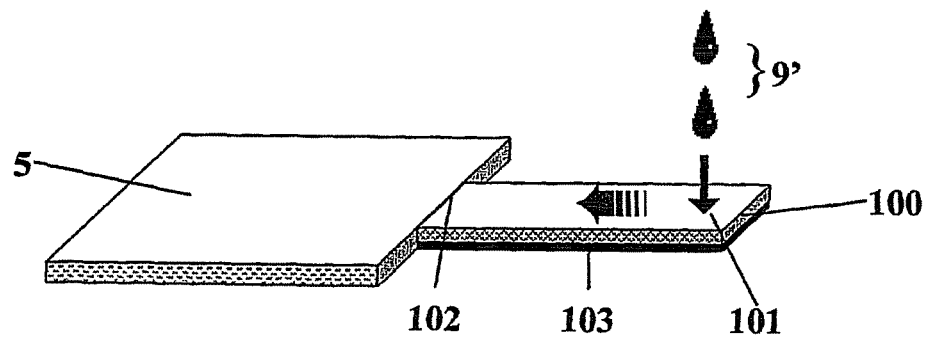
FIG. 6 is a diagrammatic illustration of a second embodiment of a portion of the test unit comprising a material defining the blood separation zone in fluid communication with the reaction zone.

To facilitate the detection of a target analyte in a whole blood sample, an alternate embodiment of the present invention provides a test unit having a blood separation zone capable of receiving and separating the fluid portion of a whole blood sample from the red blood cells (RBC), while transporting the RBC-free fluid portion, including any analyte, to the reaction zone for direct analysis. As shown in FIG. 6, the blood separation zone 100 is preferably an elongate strip of porous material which is selected on the basis of having intrinsic properties which enable it to preferentially entrap or retain the red blood cells in the sample 9' as the fluid portion migrates in a lateral direction towards the reaction zone 5. Although the shape and dimensions are not critical, preferably the blood separation zone 100 is a rectangular form having dimensions suitable for allowing efficient removal of a substantial amount of red blood cells from the whole blood sample 9' prior to the RBC-free fluid portion of the sample 9' arriving at the reaction zone 5. Thus, in effect, the blood separation material functions as a lateral flow material for the selective removal of an effective amount of red blood cells from the whole blood sample 9' so as to avoid interference with the visual detection of the analyte, while allowing other components of the sample, including any analyte, to flow with relatively unimpaired movement to the reaction zone 5. Preferably, a hydrophobic carrier 103 is affixed to the lower surface of the blood separation zone 100 to provide support and reduce seepage of the fluid phase while the RBC-free fluid portion of the whole blood sample migrates towards the reaction zone 5. The carrier 103 is preferably similar in shape and size to the blood separation zone 100.

A first end 101 of the blood separation zone 100, located a short lateral distance from the reaction zone 5, defines a region for receiving the whole blood sample 9' prior to introduction of the analyte at the reaction zone 5. A second end 102 of the blood separation zone 100 is contiguous with and may overlap slightly with the reaction zone 5, so as to be in direct fluid communication with the reaction zone 5, thereby promoting the capillary movement of the RBC-free fluid portion of the blood sample 9' from the first end of the blood separation zone 100 to the reaction zone 5. The blood separation zone 100 and the reaction zone 5 must contact one another in order to ensure optimal transfer of the sample from one zone to the other. Therefore, it is preferably that the blood separation zone 100 and the reaction zone 5 overlap with one another slightly as opposed to being abutted to one another.

Thus, the two-step assay protocol optionally employs a simultaneous separation of red blood cells from a whole blood sample 9' in order to permit testing for a desired analyte without the requirement for additional steps. For example, in the case where a whole blood sample 9' contains analyte, the sample 9' is simply applied to the first end of the blood separation zone 100 of the test unit, rather than the reaction zone 5. As the RBC-free fluid portion of the blood sample 9' migrates in a lateral direction to arrive at the reaction zone 5, the free analyte eventually comes into contact with available sites of attachment on the capture reagent and forms a complex. Thus, similar to the method steps shown in FIG. 2, unbound non-essential components are drawn into the absorbent zone located beneath the reaction zone. The label zone of the dried indicator reagent delivery unit is subsequently brought into fluid communication with the reaction zone of the test unit prior to the addition of the multifunctional buffer. Immediately following resolubilization of the dried indicator reagent by the buffer, the indicator reagent is transported to the reaction zone of the test unit, where it will bind with any target analyte that has complexed with the capture reagent. The binding reaction of the indicator reagent with the target analyte produces a visually detectable signal thereby indicating a positive result that is easily observed following removal of the dried indicator reagent delivery unit.

3.2 Competitive Technique

Those skilled in the art can deduce the application of the present invention in competitive, as well as noncompetitive (e.g. sandwich), assays for target analyte of suitable interest. In the competitive format, it is an ancillary first specific binding member of the indicator reagent (as opposed to an ancillary second specific binding member in the case of the "sandwich" technique) which is capable of binding to the second specific binding member, i.e. the capture reagent. In other words, ancillary first specific binding member of the indicator reagent competes with the target analyte, i.e. first specific binding member, for binding to sites of attachment of the capture reagent. The ancillary first specific binding member will comprise, for example, an analogue or other authentic sample of the target analyte which has comparable binding affinity with the first binding member. When the fluid test sample is deposited on the reaction zone, any target analyte, if present, will bind to available sites of attachment of the capture reagent, i.e. the second binding member, and thus potentially block the ancillary first binding member of the indicator reagent from binding to the capture reagent following its addition. If the fluid test sample happens to contain the target analyte, the absence of a color signal will indicate a positive result due to the inability of the indicator reagent to bind to the capture reagent. Alternatively, if the test sample does not contain any target analyte, the presence of a color signal will indicate a negative result due to the ability of the indicator reagent to bind to unoccupied sites of attachment of the capture reagent.

4.0 Test Unit

As described above, the diagnostic device of the present invention comprises, as a first component, a test unit having a reaction zone containing immobilized capture reagent that can specifically recognize and bind to the target analyte, an absorbent zone supporting the reaction zone, and optionally, a blood separation zone in lateral fluid communication with the reaction zone. The reaction zone of the test unit is oriented so that the label zone of the dried indicator reagent delivery unit can be brought into transient fluid communication therewith shortly after the fluid test sample is applied to the test unit.

4.1 Reaction Zone

The term "reaction zone" is intended to include the porous material to which the capture reagent and other molecules employed in the analytical assay are bound as well as additional porous supporting material, if any, that forms the lower surface of the reaction zone.

The selection of the material for the reaction zone is not critical to the invention. The materials used to fabricate the device of the present invention are well known in the art. Porous materials, such as those described in U.S. Pat. Nos. 4,670,381, 4,632,901, 4,666,863, 4,459,361, 4,517,288, and 4,552,839, may be composed singly or in combination of glass fibers, cellulose acetates, nylon, or various synthetic or natural materials.

The preferred material of the reaction zone is a membrane which has a pore size permitting separation and filtration of other non-essential components from the fluid test sample being assayed. The flow of the aqueous reagents is controlled through diffusion and the membrane should have low non-specific binding for the indicator reagent before or after treatment with reagents such as proteins, detergents, or salts. There are many porous membrane, films, or papers available commercially which have controlled hydrophobicity and are suitable for the practice of the invention. The reaction membrane can be any shape and thickness but usually is flat and thin. The absorption, diffusion or filtration of the liquid phase of the reactants from the solid phase particles in the separation step of the assay can be facilitated by the addition of a fibrous or hydrophilic material (absorbent pad) in contact with the underside of the reaction membrane. The size of the area exposed to the solid phase particles can be controlled by using a hydrophobic material such as plastic, plastic laminate, or other similar substance that is placed in contact with the reaction membrane and seals the reaction zone such that only a surface area no greater than about 150 mm$^2$ is exposed to the particulate solid phase.

The porosity of the membrane has a large influence on the flow rate of the liquid and sensitivity of the assay. The larger the pore size of the membrane, the faster the flow rate for a given liquid. As the flow rate increases, the interaction time available between the target molecule in the sample and the receptor immobilized on the reaction membrane decreases, thus decreasing assay sensitivity. Additionally, larger pore sizes provide less surface area for immobilizing the receptor molecule, which is another parameter attributable to decreased assay sensitivity. For most assays, the porosity of the membrane is preferably in the range of about 0.1 to about 12.0 microns, and more preferably ranging from about 0.2 to 0.8 microns.

The wicking power of the membrane may also affect assay sensitivity and depends on the thickness and nature of the membrane material. Wicking power can be measured as the migration of a standard solution through a certain distance per unit time. Often times, selecting a membrane having a relatively low wicking power can increase assay sensitivity. Thus, in addition to porosity, the overall thickness of the reaction membrane may affect assay sensitivity and therefore, must also be considered.

The thickness of the reaction membrane, which is the distance between the upper and lower surfaces of the reaction membrane, can vary depending upon the flow characteristics needed for a given diagnostic assay. Typically, the thickness will range from about 0.05 mm to about to 3.0 mm, and more commonly from about 0.1 to about 1.0 mm. With some immunoassays in particular, it has been found that when the thickness of the reaction membrane is greater than about 0.1 mm, and preferably in the range of about 0.2 mm to about 1.0 mm, higher sensitivity can be achieved. Moreover, it is believed that prior art devices which have relatively thin reaction membranes, such as nitrocellulose membranes less than 0.1 mm thick and which are not paper-backed, tend to allow the sample to flow sideways across the reaction membrane rather than downwards through the middle of the reaction membrane. On the other hand, a thicker reaction membrane may allow more capture reagent to be available for binding to the target analyte, thereby providing a further increase in assay sensitivity. Thus, the thickness of the membrane should be selected so that an adequate amount of binding reagent can be immobilized to capture the sample component. However, if the membrane thickness is to large, it may cause undue delay of the passage of the fluid test sample through the membrane.

Another factor to be considered is that the material of the reaction membrane be selected on the basis that it is compatible for immobilization of the capture reagent. The reaction membrane may be any suitable porous material capable of immobilizing the capture reagent employed in the diagnostic assay so long as the performance of the assay is not adversely affected. Suitable materials include nitrocellulose (supported or unsupported), glass fiber, polyester, cellulose nitrate, polyester, polycarbon, nylon, and other natural and synthetic materials which can be coupled directly or indirectly to the selected capture reagent. Usually the membrane will comprise negative charges that allow the capture reagent molecule to bind. Certain membrane materials which are charged include cellulose nitrate which has partial negative charges contributed by the nitro groups.

In some cases commercial filters are available that have immobilized to their internal and/or external surfaces a reactant for the attachment of biological molecules, such as antibodies or antigens, to the surfaces. Examples of various filters include cellulosic filters (filter papers), polyamide membranes (e.g. numerous variations of polyamide membranes are manufactured by the Pall Corporation), and various other microporous membranes, such as those available commercially from Amicon, Geleman, and Schleicher & Schuell. For example, the following membranes are available from Pall Corporation: Biodyne®, a N66 polyamide microporous membrane (U.S. Pat. No. 4,340,479 issued to Pall); Carboxydyne®, a hydrophilic, microporous, skinless nylon 66 membrane with control surface properties characterized by carboxyl functional groups at its surfaces; and Immunodyne™, a modified Carboxydyne® membrane prepared by treating a Carboxydyne® membrane with trichloro-s-triazine. Other microporous membranes, prepared by the Millipore Corporation, are described in U.S. Pat. Nos. 4,066,512 and 4,246,339.

Other materials may be pre-treated to provide a charged membrane. For example, polyester can be derivatized with carboxyl or amino groups to provide either a negatively or positively charged membrane. Nylon can be treated with acid to break peptide bonds to provide positive charges (from the amine groups) and negative charges (from the carboxyl groups).

A preferred material for utilization as a reaction membrane is a nitrocellulose membrane backed with porous paper similar to filter paper, or other types of nitrocellulose membranes with similar characteristics. A representative example is commercially available under the trade name BAC-T-KOTE by Schleicher and Schuell. This material is substantially more durable than nitrocellulose alone and can be employed without any other support component while allowing for easier handling and device assembly. Additionally, it has been found that analytical devices employing paper-backed nitrocellulose for the reaction zone have enhanced sensitivity in certain immunoassays.

Other commercially available materials are from EY Laboratories Inc. (San Mateo, Calif.; Cat. Nos. PBNC15-1, PBNC15-10, PBNC15M-1, and PBNC15M-10).

4.2 Immobilization of the Capture Reagent

In a typical system, the capture reagent is immobilized on the porous membrane of the reaction zone which will specifically recognize and bind to any target analyte present in the fluid test sample being assay. Such reagent, typically an immunological protein such as an antibody or antigen, can be immobilized directly or indirectly onto such materials, such as nitrocellulose, by either absorption, adsorption, or covalent bonding. When a fluid test sample suspected of containing the target analyte of the specific binding interaction is applied to the reaction zone containing the immobilized capture reagent, it becomes non-diffusively bound to the reaction zone. Thus, by appropriate application of a fluid test sample suspected of containing the target analyte of interest, a high concentration of the target analyte can be obtained in a well defined region within the center of the reaction zone. In appropriate cases, the capture reagent may be coated on the upper surface of the reaction zone or be a particulate which is entrapped within the matrix of the porous material of the reaction zone. Therefore, as used herein, the term "immobilized" is intended to embrace any means for fixing the capture reagent to the porous material.

A first step of the present method is to immobilize the capture reagent within a finite zone of the reaction zone. Immobilization can be accomplished by methods such as adsorption, absorption, evaporative deposition from a volatile solvent solution, covalent bonding between the capture reagent and the reaction membrane, or immunological immobilization. Covalent bonding may, for example, involve bonding the capture reagent to the reaction zone through a coupling agent, such as a cyanogen halide, e.g. cyanogen bromide or by the use of gluteraldehyde, as described by Grubb, et al. in U.S. Pat. No. 4,186,146. Immunlogical immobilization to the reaction membrane may be by absorption, or by covalent linkage, directly, or through a linker of sorts well-known to those skilled in the art. Suitable methods of carrying out these procedures are given, for example, by !man and Hornby in Biochemical Journal (Volume 129; Page 255; Campbell, Hornby, and Morris in Biochem. Biophys. Acta (1975), Volume 384; Page 307; and Mattisson and Nilsson in F.E.B.S. letters, (1977) Volume 104, Page 78. See also, for example, U.S. Pat. Nos. 4,376,110 and 4,452,901. In addition, chemically pretreated materials suitable for coupling antibodies can be purchased commercially.

Immunological immobilization is preferred for the practice of the present invention. For example, if a sandwich immunoassay is employed in the present device using antibody as the capture reagent, then the reaction membrane is impregnated with antibody by way of absorption using a dispenser/printer technique (BioDot, Calif., U.S.A.). This involves applying one or more distinct antibodies to the membrane by spraying them directly onto a reaction membrane. The above technique is most readily achieved using a commercial printing device termed a BIOJET QUANTI 3000, and provides a stream of the immunological protein under a variety of conditions, and at varying stream widths. Using this technique, it is possible to rapidly deposit a series of lines, or other discrete patterns on the reaction membrane, each containing an antibody with different antigenic specificities for binding one or more antigens. Thus, the number of antigens that can be assayed is a function of the number of different antibodies that can be applied in distinct patterns.

Depending on the detection limits the user wishes to impose on the diagnostic assay, the capture reagent can be deposited singly or in various combinations in the reaction zone in a variety of configurations to produce different detection or measurement formats. For example, a panel of two or more different specific binding members selected as the capture reagent for the diagnostic assay may be applied to different regions of the same reaction membrane so that the presence of multiple analytes in a single fluid test sample may be simultaneously analyzed, e.g. for the detection of HIV and HCV. Preferably, the capture reagent is deposited in a discrete test zone having an area substantially smaller than that of the entire surface area of the porous material used in the reaction zone. Various patterns that are convenient for the distribution of the capture reagent may include, but are not limited to, numerals, letters, dots, lines and symbols, or the like, which display the detectable signal upon completion of the assay. It is preferred that the pattern of the discrete test zone be in the form of a single line to enhance the visibility of the test result.

4.3 Capture Reagent

Since the present apparatus is designed to be used in a method for detecting a target analyte in a fluid test sample, a capture reagent must be provided which will recognize and be capable of specifically binding to the target analyte. One of ordinary skill in the art will appreciate that the term "specific binding" refers to the interaction that will occur between two or more complementary non-identical components to form a complex. Examples of such binding pairs include antigens and antibodies, hormones (and other intracellular messengers) and cell receptors, sugars and lectins. Either member of the specific binding pair can be immobilized to the reaction zone with the other member being the analyte being detected in the test sample. Exemplary, but not exclusive of the present invention, is the specific binding interaction that occurs as a result of antibody-antigen interactions. However, it should be realized that the use of terms such as antigen and antibody are not mutually exclusive since antibodies can act as antigens for other antibodies.

Because of the relative ease with which specific antibodies can now be prepared against antigens, preferred embodiments of the invention may or can use monoclonal antibodies attached to the reaction membrane to detect the presence of their specific antigen in a fluid test sample. The monoclonal antibodies can belong to any of the classes or subclasses of antibodies, including IgA, IgD, IgE, IgG (subclasses 1-4, if human; 1, 2a, 2b, 3, if murine), or IgM. Actively binding fragments of antibodies can also be employed, such as Fab, Fv, F(ab')$_2$, or the like. The preparation of monoclonal antibodies is well known in the art which is accomplished by fusing spleen cells from a host sensitized to the antigen with myeloma cells in accordance with known techniques or by transforming the spleen cells with an appropriate transforming vector to immortalize the cells. The cells can be cultured in a selective medium, cloned, and screened to select monoclonal antibodies that bind the designated antigens. Numerous references can be found on the preparation of monoclonal and polyclonal antibodies (e.g. Kohler and Milstein, (1975) Nature (London) 256, 495-497; Kennet, R., (1980) in Monoclonal Antibodies (Kennet et al., Eds. pp. 365-367, Plenum Press, N.Y.).

4.4 Control Zone

In addition to the capture reagent, a defined area of the exposed reaction zone may also contain a control molecule. In this regard, color development at the test site may be compared with the color of one or more standards controls to determine whether the reagents are stable and the test is performing properly. In general, when testing for the presence of target analyte, the diagnostic device will have a built-in control of an antibody directed to human immunoglobulin G (IgG), IgM, IgE, or IgA. Thus when a fluid test sample is added to the diagnostic device, immunoglobulin will bind to the control region regardless of whether or not target analyte happens to be present in the sample. For example, a suitable control may be established by using Protein A which is disclosed in U.S. Pat. No. 5,541,059 (Chu). Other suitable controls are well known in the art.

4.5 Blocking the Reaction Zone

As noted above, the capture reagent, and the optional use of controls, are typically applied only to defined regions of the exposed surface of the reaction zone. The capture reagent will often be applied to a region within the center of the reaction zone such that the perimeter of the exposed surface of the reaction zone will not have any capture reagent bound thereto. On the other hand, in some situations, it may be appropriate to cover the entire exposed surface of the reaction zone with the capture reagent. If, however, capture reagent is immobilized onto a limited region of the exposed surface of the reaction zone, the porous material or membrane from which the zone is made can be treated with a blocking composition that prevents the target analyte and other components of the sample from non-specifically binding to the reaction zone. For assays where non-specific binding is not problematic, a blocking step will be unnecessary. Also, the use of a good quality paper-backed nitrocellulose may make a blocking step unnecessary in some assays. However, if a blocking step is needed, common blocking solutions comprising bovine serum albumin (BSA) or other proteins which do not interfere with, or cross-react with, reagent materials of the assay can be used. BSA is usually used in amounts from about 1 to 10%.

The blocking treatment typically occurs after the analytical device has already been assembled and the capture reagent is immobilized to the reaction zone. A sufficient amount of blocking composition which will cover the exposed surface of the reaction zone is applied. After the blocking composition has dried, the analytical device is ready for use.

4.6 Absorbent Zone

The sensitivity of reaction-membrane type immunoassays (i.e. the ability to detect very low levels of target substance) can be increased if the sample is concentrated through the reaction zone. With some devices, concentration of the sample through a reaction zone is achieved by having an absorbent material, or pad, beneath the reaction zone that draws the sample, which is added to the surface of the reaction zone, through to the absorbent material below. The absorbent zone can be generated from any material capable of wicking fluid by way of capillary action, such as cotton or paper. Membrane-based immunoassays that utilize various absorbent materials to concentrate sample are exemplified in U.S. Pat. Nos. 5,185,127, 5,006,464, 4,818,677, 4,632,901, and 3,888,629.

An absorbent material is situated underneath the lower surface of the reaction zone so as to be in direct fluid communication with the reaction zone. Thus, the upper surface of the absorbent material is immediately adjacent to the lower surface of the reaction zone. Fluid communication contact involving direct physical contact of the absorbent material with the reaction zone may optionally include the separation of a portion of the absorbent material from the reaction zone by an intervening spacer layer which has an opening therein. Accordingly, the spacer layer still permits direct contact between the reaction zone and the absorbent zone thereby enabling the assay reagents to flow uniformly from the upper surface down to the lower surface of the assay apparatus. Although not critical to the performance of the apparatus, the spacer layer also serves to hold the porous membrane of the reaction zone. The spacer layer may be made of any rigid or semi-rigid material that does not bind or interact with assay reagents used in conjunction with the invention. Exemplary of materials for the spacer layer 25 are fiberglass, paper, hydrophilic polypropylene, or cellulose. The thickness of the spacer layer 26 will generally be in the range of about 0.1 mm to 1 mm. In embodiments of the invention where ease of manufacture and reduced costs are desired, the upper surface of the absorbent material is typically placed immediately adjacent the lower surface of the reaction zone.

The selection of material for the absorbent zone is not critical and a variety of fibrous filter materials can be used, including one or more layers of the same or different materials, providing that the material selected is compatible with the target analyte and the assay reagents. Any conventionally employed absorbent material that is capable of drawing or wicking fluid through a porous membrane, such as for example, by capillary action, can be used in the present invention. The absorbent material should be capable of absorbing a volume of fluid test sample that is equivalent or greater than the total volume capacity of the material itself. Useful known materials include cellulose acetate fibers, polyester, polyolefin or other such materials. The absorbent material provides a means to collect the sample by providing uniform "suction" to deliver the sample from the well, through the reaction zone, and down into the absorbent material. Thus, the absorbent body also acts as a reservoir to hold the sample, and various reagents that are used when the assay is performed. Accordingly, when used in assays where relatively large volumes of fluid are used, the absorbent material should have high absorbent capacity so as to prevent or minimize the possibility of back-flow of sample and reagents from the absorbent body back into the reaction membrane.

As with the reaction zone material, the wicking power of the absorbent material can be an important parameter. Wicking time is defined in terms of the time required for water to travel a defined distance through the absorbent material and is related to the thickness and porosity of the material. Wicking power can vary greatly from one material to the next and therefore, the properties of the analytical device and flow rate of sample and reagents can be modified by varying the absorbent material used.

4.7 Blood Separation Zone

To facilitate the detection of a target analyte in a whole blood sample, an alternate embodiment of the present invention provides a test unit capable of receiving and separating the fluid portion of a whole blood sample from the red blood cells (RBC) featuring a blood separation zone in lateral fluid communication with the reaction zone. The blood separation zone functions to selectively retain cellular components (i.e. red blood cells) contained within the whole blood sample and deliver the remaining components of the RBC-free fluid portion of the blood sample, including any analyte, to the reaction zone for eventual analysis. This particular feature is useful in preventing any interference during visualization of a color reaction for the detection of analyte and avoids the necessity of obtaining a preliminary extraction of serum or plasma in settings where proper equipment to perform such a procedure is unavailable.

Various methods for the separation of blood cells from the fluid portion of blood are described using separation coatings, erythrocyte aggregating and agglutinating agents, materials having asymmetric pore sizes, polymer-containing matrixes, and multilayer systems, to name a few, e.g. U.S. Pat. Nos. 3,768,978 to Grubb et al., 3,902,964 to Greenspan, 4,477,575 to Vogel et al., 4,594,372 to Zuk, 4,753,776 to Hillman et al., 4,816,224 to Vogel et al., 4,933,092 to Aunet et al., 5,055,195 to Trasch et al., 5,064,541 to Jeng et al., 5,076,925 to Roesink et al., 5,118,428 to Sand et al., 5,118,472 to Tanaka et al., 5,130,258 to Makino et al., 5,135,719 to Hillman et al., 5,209,904 to Forney et al., 5,212,060 to Maddox et al., 5,240,862 to Koenhen et al., 5,262,067 to Wilk et al., 5,306,623 to Kiser et al., 5,364,533 to Ogura et al., and 5,397,479 to Kass et al.

In a preferred embodiment, the blood separation zone is an elongate or rectangular strip of porous material having intrinsic physical properties which enable it to preferentially and sufficiently entrap or retain the red blood cells in the sample within the blood separation zone. A first end of the blood separation zone, located a short lateral distance from the reaction zone, defines a region for receiving the whole blood sample during the first step of the assay protocol, and prior to introduction of the target analyte at the reaction zone. A second end of the blood separation zone, in direct fluid communication with the reaction zone, helps to promote the movement of the RBC-free fluid portion of the blood sample from the first end of the blood separation zone to the reaction zone for eventual analysis. The blood separation zone and the reaction zone must contact one another in order to ensure optimal transfer of the sample from one zone to the other. Accordingly, the materials selected for the blood separation zone and the reaction zone may overlap slightly with one another in order to ensure adequate migration of the RBC-free portion of the whole blood sample.

A variety of materials can be used for the blood separation zone such as glass fiber, glass fiber/cellulose mixtures, cellulose, or other proprietary materials, including synthetic materials, e.g., nylon. Preferably, a permeable glass fiber matrix is employed as the blood separation material to facilitate the separation of red blood cells from whole blood. A variety of grades of different thicknesses and absorbencies of glass fiber materials are commercially available to facilitate blood separation and include, for example, GF-24, GF-25, and #33, available from Schleicher & Schuell (Keene, N.H., U.S.A.); G143, G144, and G167, available from Ahlstrom (Mount Holly Springs, Pa., U.S.A.); GFQA30VA, GF/P 30, GF/DE 30, GF/SE 30, GF/CM30VA, GF/CM 30, F 075-14, F487-09, GF DVA, GFVA 20, and GD-2, available from Whatman (Fairfield, N.J., U.S.A.).

Useful glass fiber/cellulose mixture materials include F255-07 90 glass/10 cellulose, F255-09 70 glass/30 cellulose, F255-11 50 glass/50 cellulose, and F255-12 50 glass/50 cellulose, available from Whatman.

Useful cellulose materials include 598, available from Schleicher & Schuell. Miscellaneous or other materials falling outside the above categories can also be used, including HemaSep V and Leukosorb; which article of manufacture according to the subject invention available from Pall Bio-Support (Port Wash., N.Y., U.S.A.).

One useful nylon material is Nylon 6.6 Transfer Membrane, which is commercially available under the tradename Biodyne B (Pall Specialty Materials, Port Wash., N.Y.). In addition, the material known as "PlasmaSep", available from Whatman, can be used.

Although the shape and dimensions of the blood separation zone are not critical, preferably it has a narrow rectangular form and dimensions suitable for allowing efficient removal of a substantial amount of red blood cells from the whole blood sample during migration of the fluid portion of the sample from the first end to the second end of the zone. Thus, in effect, while a narrow rectangular shape is preferred to channel fluid portion of the blood sample to the reaction zone, the dimensions may vary depending on the intrinsic properties (e.g. absorbency, migration rate, etc.) of the material selected for the blood separation zone. In a preferred embodiment, the blood separation zone is made using the glass fiber material F487-09, available from Whatman, having dimensions between approximately 4 to 7 mm in width, between approximately 10 and 15 mm in length, and between approximately 0.2 mm and 1.0 mm in thickness. More preferably, the blood separation material is about 7 mm in width by about 10 mm in length and about 0.5 mm in thickness. These dimensions are optimized to be capable of receiving and separating the total volume of a whole blood sample, e.g. two drops of blood.

The blood separation material preferably has a rigid or semi-rigid carrier or backing affixed to its lower surface to provide support and reduce seepage of the RBC-free fluid portion of the whole blood sample while it migrates towards the reaction zone. Suitable materials for use as a carrier or backing include, for example, hydrophobic materials such as polycarbonate, polyethylene, Mylar, polypropylene, vinyl, cellophane and polystyrene, etc. as well as water-proofed or fluid-resistant cardboard or similar materials. The carrier or backing may be affixed either directly or indirectly to the blood separation material by means of a fluid-resistant adhesive.

Suitable adhesives are well-known in the art. The carrier may be of any shape and of almost any size which may conveniently be handled. However, the carrier is preferably similar in shape and size to the blood separation material. Thus, the carrier is preferably formed as an elongate or rectangular strip having a length and width similar to or the same as the blood separation material.

5.0 Dried Indicator Reagent Delivery Unit

As discussed above, the diagnostic device of the present invention comprises, as a second member, a dried indicator reagent delivery unit comprising a label zone permeated with a dried indicator reagent.

The selection of the material for the label zone is not critical and can be any suitably absorbent, porous or capillary possessing material through which the multifunctional buffer and resolubilized indicator reagent may be transported by wicking action. The criteria of selection is that the material allow for the resolubilization and mixing of the dried indicator reagent upon addition of the multifunction buffer, as well as initiate the transfer of the buffer and freshly dissolved indicator reagent to the reaction zone of the test unit.

Natural, synthetic, or naturally occurring materials that are synthetically modified, can be used as a filter medium including, but not limited to cellulose materials such as paper, cellulose, and cellulose derivatives such as cellulose acetate and nitrocellulose, fiberglass, cloth, films of polyvinyl chloride, and the like. Although a preferred filter medium is nitrocellulose, the material should be chosen for its ability to release the indicator reagent upon reconstituting with the multifunctional buffer. Moreover, the fluid flow through the filter medium should be laminar as opposed to turbulent flow characteristics which adequately allows for initial mixing of the buffer with the indicator reagent.

5.1 Indicator Reagent

The use of indicator reagents to detect the presence of a target analyte in a test sample is well known in the art. Depending on the type of diagnostic assay employed, the label employed in the indicator reagent is conjugated to a specific binding member or general marker protein (e.g. Protein A, Protein G, anti-IgG) that will directly, or indirectly, bind to the target analyte. Formation of an indicator reagent between a specific binding member and a label may be any of the conventional types including metal complex labels, radioactive labels, enzyme labels, fluorescent labels, radioactive labels, chemiluminesct labels, and the like.

An important consideration in the design of a rapid diagnostic device is that the label chosen in the generation of the indicator reagent should give rise to a readily detectable signal, e.g. a strongly-coloured area easily detectable by the eye. Thus, an important preferred embodiment of the invention is the use of "direct labels", attached to one of the specific binding members. Direct labels are well known in the art and highly advantageous for their use in rapid diagnostic systems. Examples of direct labels include, but are not limited to metal sols, non-metal sols, dye sols, latex particles, carbon sol, and liposome contained colored bodies. Some of their advantages are that they can be used to produce a visually detectable signal without the need to add further reagents, are readily visible to the naked eye without the aid of instrumentation, and can be readily used in a diagnostic device since they are stable when stored in the dry state. With respect to the latter, their stability and immediate release on contact with a buffer reagent can be accomplished by the use of soluble glazes. In view of the above comments, indirect labels, such an enzymes, e.g. alkaline phosphatase and horseradish peroxidase, are less preferred because they usually require the addition of one or more substrates before a visible signal can be detected.

Non-metal sols, such as those of selenium, tellurium and sulfur may be produced according to the methods described in U.S. Pat. No. 4,954,452 (Yost, et al). Dye sol particles may be produced as described by Gribnau et al., in U.S. Pat. No. 4,373,932 and May et al., WO 88/08534, dyed latex as described by May, supra, Snyder, EP-A 0 280 559 and 0 281 327, and dyes encapsulated in liposomes by Campbell et al., U.S. Pat. No. 4,703,017. The use of polymerized dye materials in colloidal form for specific binding assays is also described by in U.S. Pat. No. 4,166,105 by Hirschreid which relates to labeled specific binding reagents reactive with specific antigens prepared by linking fluorescent dye molecules to analyte specific antibodies through polymers comprising reactive functional groups. Also of interest is U.S. Pat. No. 4,313,734 by Leuvering relating to metal sols; Leuvering, et al., "Sol Particle Immunoassay (SPIA)", Abstract, Journal of Immunology, 1(1), pp. 77-91 (1980); Leuvering Dissertation (1984), Sol Particle Immunoassay (SPIA): The Use of Antibody Coated Particles as Labeled Antibodies in Various Types of Immunoassay; Uda et al., Anal. Biochem. 218 (1994), 259-264, DE-OS 41 32 133, page 3, lines 16-18, for applications as markers and Tang et al., Nature 356 (1992), 152-154; Eisenbraun et al., DNA and Cell Biology 12 (1993), 791-797. Furthermore it is also known that non-metallic colloidal particles such as carbon particles (van Amerongen, Anabiotic '92 (1993), 193-199) can also be used. Moeremans, et al., EPO Application No. 158,746 discloses the use of colloidal metal particles as labels in sandwich blot overlay assays. At present colloidal gold particles are used most frequently.

Among the direct labels, metallic sols are preferred, more preferably gold sol particles such as those described by Leuvering in U.S. Pat. No. 4,313,734. Leuvering discloses the use of metal sol particles as labels for in vitro determination of immunological components in an aqueous test medium. Specifically disclosed are immunoassay test kits for the detection of antigens or antibodies employing one or more labeled components obtained by coupling the component to particles of an aqueous sol dispersion of a metal, metal compound or polymer nuclei coated with a metal or metal compound having a particle size of at least 5 nm.

The metal sol particles to be used in accordance with the present invention may be prepared by methods which are well known in the prior art. For instance, the preparation of gold sol particles is disclosed in an article by G. Frens, Nature, 241, 20-22 (1973). Additionally, the metal sol particles may be metal or metal compounds or polymer nuclei coated with metals or metal compounds, all as described in the Leuvering patent mentioned above. In this regard, the metal sol particles may be of platinum, gold, silver or copper or any number of metal compounds which exhibit characteristic colors.

5.2 Colloidal Gold Particles

Colloidal particles which are suitable as labels according to the invention include those which may be conjugated to specific binding members or general marker proteins without interfering with the activity of such reagents or with other reagents or analytes.

Colloidal metal particles are particularly suitable as labels according to the present invention and include those particles which are comprised of metals or metal compounds selected from the group consisting of the metals platinum, gold, silver and copper and the metal compounds, silver iodide, silver bromide, copper hydroxide, iron oxide, iron hydroxide or hydrous oxide, aluminum hydroxide, or hydrous oxide, chromium hydroxide or hydrous hydroxide, lead sulfide, mercury sulphide, barium sulphate and titanium dioxide. Preferred colloidal metal particles include those made up of gold.

Colloidal gold particle markers are simple to use in comparison to other conventional markers. For example, they do not require instruments necessary for detection of other markers such as radioactive isotopes and unlike enzymes, they do not require the additional step of adding a substrate.

Colloidal gold particles may be produced according to methods generally known in the art. Of interest to the present invention are those references relating to the use of dispersions of colloidal particles in immunological assay procedures. Specifically, Frens, Nature, 241, 20-23 (1973) discloses methods for the production of gold sol particles of varying sizes through the reduction of gold chloride with aqueous sodium citrate. The colors of the visually detectable signal from the metal particle label is dependent upon the identity and particle size of the metal particle which may be controlled by varying the concentration of the reactants. For example, colloidal gold particles produce colors ranging from orange to red to violet depending upon the particle size of the sol.

The colloidal gold reagent is selected for its unusual properties including the ability to intensify color to the naked eye when concentrated on solid surfaces, to minimally bind non-specifically to solid surfaces, to be prepared in relatively uniform particle sizes, and to be easily lyophilized and resolubilized. Colloidal gold particles can be prepared in a number of ways through the reduction of tetrachloroauric acid which produces a variety of particle sizes ranging from 5 nm to 100 nm. The preferred particle sizes are from 15 to 20 nm. The colloidal gold particles can have an intermediary binder absorbed to its surface prior to the addition of the binding substance, but direct attachment is satisfactory. Absorbing the selected binding substance is achieved by carefully controlling concentrations, ionic strength and pH of the reaction mixture. The choice of method of producing the colloidal gold raw material or the method of attaching the binding substance are well known to those skilled in the art. After the labeling with colloidal gold is complete, the reagent is differentially centrifuged or filtered to control particle size. Particle sizing by gel filtration methods are also well known. The colloidal gold labeled reagent can be used as a colloidal suspension or as a lyophilized reagent with or without the presence of the aforesaid solid phase particles as an indicator reagent.

The resulting coated and stabilized colloidal metal particles may then be conjugated with various proteins. Any protein which may be subjected to freeze-drying or other forms of drying such as by incubator, air-drying and spray drying may be applied in the present invention. Exemplary of protein for use in the present invention includes, but is not limited to, polyclonal or monoclonal antibodies, antigen, lectin, protein A, protein G, bacterial, and the like. In those instance where an immunodiagnostic assay is a sandwich format employing an antibody as the capture reagent for the detection of an antigen as the target analyte, the binding member of the indicator reagent is usually a second antibody having specificity for antigen bound to the first antibody, but which binds to the antigen at a site apart from where the first antibody is bound. On the other hand, the binding member of the indicator reagent is usually an analogue, or other authentic example, of the antigen which can bind to the capture reagent at the same site where the target analyte binds in the case of a competitive format.

For details and engineering principles involved in the synthesis of colored particle conjugates see Horisberger, Evaluation of Colloidal Gold as a Cytochromic Marker for Transmission and Scanning Electron Microscopy, Biol. Cellulaire, 36, 253-258 (1979); Leuvering et al, Sol Particle Immunoassay, J. Immunoassay 1 (1), 77-91 (1980), and Frens, Controlled Nucleation for the Regulation of the Particle Size in Monodisperse Gold Suspensions, Nature, Physical Science, 241, pp. 20-22 (1973). Surek, et al., Biochem. and Biophys. Res. Comm., 121, 284-289 (1984) discloses the use of protein A labeled colloidal gold particles for the detection of specific antigens immobilized on nitrocellulose membranes.

5.3 Drying Process—Sugar/Glazing Treatment

According to one important aspect of the invention, the label zone of the dried indicator reagent delivery unit essentially comprises the indicator reagent impregnated and dried within the thickness of a porous material which can then be resolubilized by addition of the multifunctional buffer. Thus, by incorporating one of the assay reagents within the device of the present invention, makes possible the reduction in the number of steps required in the assay protocol by eliminating the addition and/or prior mixing of an indicator reagent.

In order to assist the free mobility of the indicator reagent when the label zone of the dried indicator reagent delivery unit is moistened with the multifunctional buffer, the dried indicator reagent delivery unit is pre-treated with a glazing material in the region to which the indicator reagent is applied. Glazing can be achieved, for example, by depositing an aqueous sugar or cellulose solution, e.g. of sucrose or lactose, on the relevant region of the dried indicator reagent delivery unit, while avoiding the remainder of the filter unit, and air drying. The indicator reagent can then be applied to the glazed portion.

The glazing process involving the use of one or more sugars (e.g. glucose, lactose, trehalose and sucrose) is highly advantageous when employing the dried indicator reagent of the present invention in that the sugar serves (1) as a protein stabilizer, (2) to improve the long term stability of the dried indicator reagent, and (3) acts as a rapid releasing agent. According to a preferred embodiment of the invention, sucrose was determined to be the best sugar compared to others in the performance of the assay because of (1) its solubility, (2) short period of drying, (3) the overall sensitivity of the assay result, (4) its use as a preservative, and (5) it is economical to use.

6.0 Buffer Reagent

Conventional diagnostic assays usually necessitate the use of two or more fluid reagents in order to perform various steps of the assay protocol including, for example, resolubilizing a dried indicator reagent, diluting a fluid test sample, blocking the membrane surface where the assay reaction takes place, facilitating transport of critical reagents and/or washing unbound reactants from the reaction zone. Since each of these steps involves the mixing or preparation of different reactants, different formulations of liquid reagents are likely required due to differing pH, ionic strength, additives, type and strength of buffer, temperature, etc. For example, the resolubilization process usually requires the use of a physiological buffer such as buffered saline or double distilled water, the blocking process uses a liquid reagent formulated with any number of animal serum albumins, gelatin or non-fat milk, and the washing and/or diluting process involves the use of a phosphate buffered saline containing different amounts of surfactant or detergent at neutral pH to remove any non-specific binding reactants. Moreover, in order to ensure that the user performs each step of the assay correctly using the appropriate liquid reagent, the reagents themselves must be clearly labeled and readily distinguished from one another, so as to avoid any possible confusion and user error.

An important aspect of the present invention overcomes the various problems described above associated with the use of several assay reagents by providing a multifunctional buffer for single utilization in the 2-step assay procedure. The multifunctional buffer is formulated to serve as a combination resolubilization reagent of the dried indicator reagent, transport facilitating reagent of resolubilized indicator reagent from the label zone of the dried indicator reagent delivery unit to reaction zone of the test unit, and washing reagent to remove unbound reactants from the reaction zone. In order to simplify the number of reagents and steps required to perform the assay, the multifunctional buffer has been specially formulated to be used in conjunction with the dried indicator reagent. It is therefore, particularly advantageous to utilize the multifunctional buffer and dried indicator reagent as a combined system since the multifunctional buffer allows optimal sensitivity and higher specificity to be achieved during performance of the assay, while additionally avoiding aggregation and inactivation of the dried indicator reagent in solution.

As will be apparent to one skilled in the art, the composition of the multifunctional buffer may vary in accordance with the requirements of the specific assay such as the particular capture reagent and indicator reagent employed to determine the presence of a target analyte in a test sample, as well as the nature of the analyte itself. In general, the multifunctional buffer will contain compounds that have primary functions in the assay with respect to their properties in serving as a diluting, washing and resolubilizing agent. However, since the reaction zone of the present invention is already pretreated with conventional blocking agents following immobilization of the capture reagent, the buffer formulation eliminates the need to include a non-specific blocking agent. A method of using the multifunctional buffer as provided by the present invention essentially involves dropwise addition of the buffer to the dried indicator reagent delivery unit in the final step of the 2-step assay to resolubilize the dried indicator reagent. A kit containing the multifunctional buffer as a component is also provided.

Accordingly, the present invention provides an improved buffer which serves as a multifunctional reagent without sacrificing either the sensitivity or specificity of the assay comprising: (1) a biological buffer to maintain the pH between about 7.0 to 10.0; (2) at least one surfactant to reduce non-specific binding of assay reagents while simultaneously avoiding inhibition of a specific binding interaction; (3) a high molecular weight polymer as a dispersing and suspending reagent having a molecular weight in a range of from about $2 \times 10^2$ to about $2 \times 10^6$ D; (4) a pH stabilizer to maintain the pH of the multifunctional buffer between about pH 7.0 to 10.0; (5) an ionic salt to reduce the non-specific binding of antibodies; (6) at least one preservative to reduce bacterial and microbial growth; and (7) a calcium chelator to prevent a whole blood test sample from clotting; wherein the biological buffer, surfactant, high molecular weight polymer, pH stabilizer, ionic salt, preservative and calcium chelator are all at effective concentrations.

The improved multifunctional buffer composition of the invention can include a conventional buffer such as a phosphate buffer, MES (morpholino-ethanesulfonic acid) buffers, BIS-TRIS buffers, citrate buffers, TRIS-HCl buffers and borate buffers, at an effective concentration which can range from about 5 to 100 mM, preferably in the range of from about 5 to 30 mM, and most preferably about 5 mM. The preferred buffer is a phosphate buffer, preferably comprising sodium phosphate, monobasic and sodium phosphate, dibasic, at concentrations such that the effective pH of the buffer is achieved. The pH of the buffer of the present invention can range from a pH of about 7.0 to a pH of about 10.0.

The biological detergents (surfactants) used in the present invention can include non-ionic surfactants, anionic surfactants, zwitterionic surfactants and cationic surfactants. The Non-ionic detergents useful in the invention include polyoxyethylene sorbitan monolaurate (Tween®20), polyoxyethylene sorbitan monooleate (Tween®80), polyoxyethylene ethers (Triton®., Brij®) and octylphenel ethylene oxide (Nonidet®). Preferably, non-ionic detergents are used. The most preferred non-ionic detergent is Triton®X-100. Non-ionic detergent acts as a dispersing agent to reduce the non-specific binding of antibodies/antigens to the reaction membrane which may occur as a result of target analyte adhering to the solid phase due to a non-specific reaction, thereby increasing the background of the assay. Although biological detergents reduce the event of such binding caused by non-polar or hydrophobic interactions, non-ionic detergents are preferred for their ability to reduce non-specific binding while avoiding the inhibition of specific binding. Effective concentrations of the biological detergent range from about 0.01 to about 0.50% (w/v), preferably range from about 0.05 to about 0.10% (w/v), and most preferably the concentration is about 0.07% (w/v).

Ionic salts provide a source of cations and anions which helps to reduce the frequency of non-specific binding of antibodies, other than analyte antibodies, caused by ionic interactions. Salts that are useful in the formulation of the multifunctional buffer reagent are NaCl and KCl, most preferably NaCl. Effective concentrations of sodium chloride range from about 0 to about 300 mM, preferably range from about 50 to about 200 mM.

The high molecular weight polymer functions as a dispersing and suspending reagent while additionally preserving the binding capacity of antibodies. Examples of high molecular weight polymers which may be used in the buffer are polyvinylpyrrolidone (PVP), dextrans, polyethylene glycol (PEG), and polyvinyl alcohol, to name a few. The preferred high molecular weight polymer for use in generating the buffer is PVP; most preferably PVP-40, at an effective concentration. Effective concentrations of PVP in the buffer of the invention range from about 0.1 to about 3.0% (w/v), preferably range from about 0.5 to about 2.5%, and most preferably the concentration is about 1.4%. The high molecular weight polymer selected for use in the invention can include PVP having molecular weights of from about 10 kD to about 1500 kD, dextrans with molecular weights ranging from about 10 kD to about 2000 kD, polyethylene glycols (PEG) having molecular weights in the range of from about 200 D to about 10,000 D, and polyvinyl alcohol having a molecular weight of about 10,000 D to about 100,000 D. Other examples of high molecular weight polymer also include polybrene (hexadimethrine bromide), methylcellulose, gum acacia, protamine sulfate, merquat, celquat and magnafloc, provided at an effective concentration.

It is preferable to include a calcium chelating agent, such as ethylenediaminetetraacetic acid (EDTA), or salts thereof, in the multifunctional buffer composition, to reduce or prevent the possible clotting of a finger-pricked whole blood test sample through the blood coagulation process. Calcium chelating agents, other than EDTA, such as citrate, citrate salts, and ethylenebis(oxyethylenenitrilo)tetraacetic acid may similarly be used. Biopolymers (i.e. non-chelating agents) such as heparin and sulfated chitosan, which will inactivate specific clotting factors within the blood coagulation process can also be used. EDTA is included in the buffer composition at an effective concentration ranging from about 5 mM to 100 mM, more preferably at about 10 mM to about 50 mM, and most preferably about 20 mM.

The pH stabilizer functions to maintain the pH of the buffer within a range of about pH 7.0 to 10.0. An exemplary pH stabilizer includes trizma hydrochloride, although other known stabilizers may also be useful in this composition. The effective concentration of trizma hydrochloride is preferably from about 20 to 30 mM.

7.0 Housing

In general, the assay composite comprising the test unit and the dried indicator reagent delivery unit can be housed in a suitable container to form an analytical apparatus. Preferably, the container should safeguard the solid phase materials and dried indicator reagent from contamination and to provide ease and convenience in handling of the assay device. Moreover, the container should be leak-proof thereby ensuring containment of fluids and their safe disposal after use.

Figure 4:
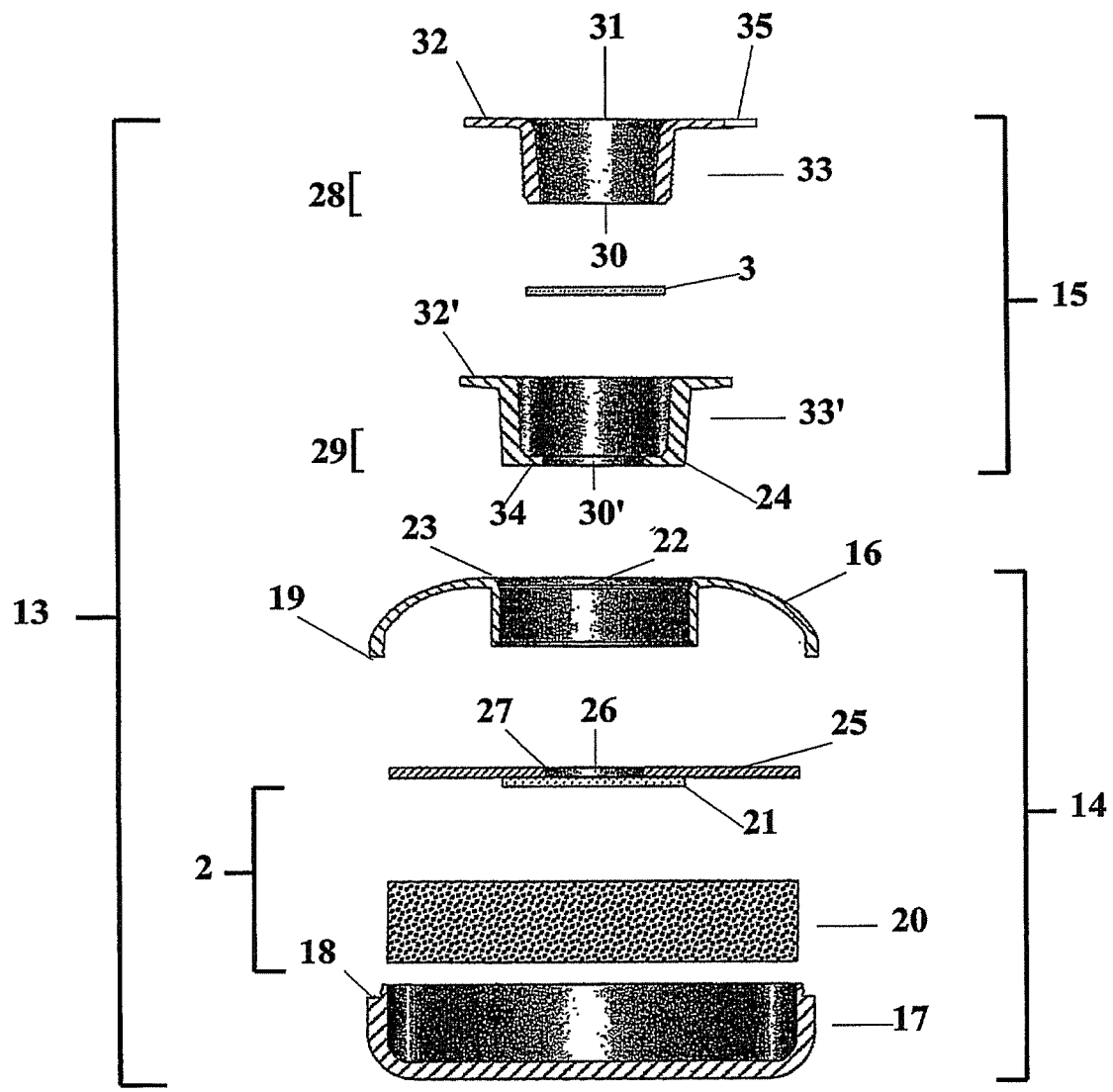
FIG. 4 shows an exploded cross-sectional view of an example of a suitable container which houses the test unit and the dried indicator reagent delivery unit.
Figure 5:
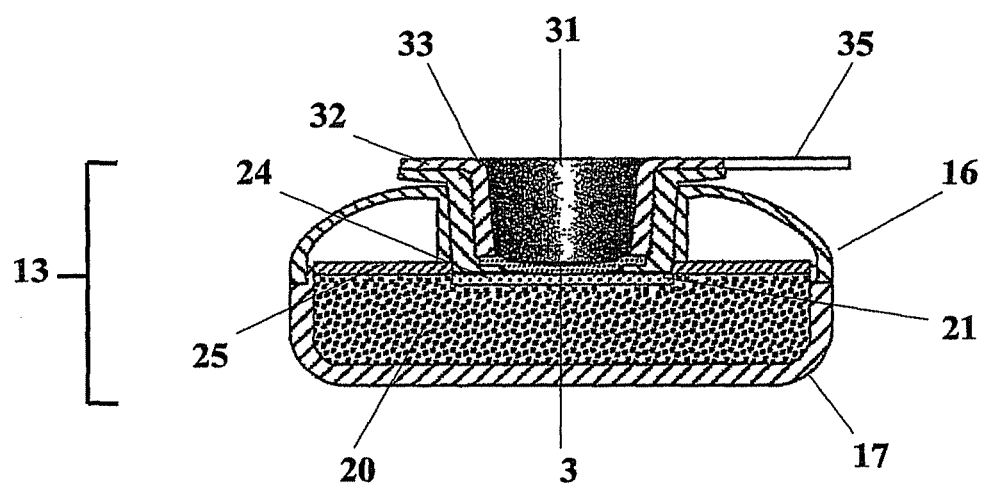
FIG. 5 shows an enlarged cross-sectional view of the container of FIG. 4 in its assembled form.

The apparatus 13 illustrated in FIGS. 4 and 5 provides a representative example of the type of container that can be included in a test kit which incorporates the flow-through device of the present invention. The apparatus 13 comprises two detachable components, namely the test cartridge 14 and the dried indicator reagent delivery cap 15, which are vertically and spatially distinct to one another when placed in transient fluid communication during the assay protocol. The housing is capable of maintaining the layers of the test unit under compression so as to provide continuous and uniform contact therebetween and so that liquid will flow uniformly through the apparatus 13. The housing will be made of an inert material conveniently being any of a variety of disposable commercial plastics which may be molded, for example, polyethylene, polypropylene, styrene, ABS, polyacrylate, polystyrene, or the like.

Although the two components of the apparatus 13 have the particular configuration and dimensions depicted therein, any other appropriate design or modifications may be employed so long as the components are still capable of being transiently connected to one another in a single movement during the assay protocol. The means of connecting the two components is not critical so long as so that they are properly aligned to effect optimal fluid communication with one another upon interconnection of the dried indicator reagent delivery cap 15 with the test cartridge 14. For example, according to the design shown in FIGS. 4 and 5, the dried indicator reagent delivery cap 15 may be frictionally fitted to the reservoir 22 of the test cartridge 14. Although not illustrated therein, the dried indicator reagent delivery cap 15 may be optionally hinged to the test cartridge 14 to avoid possible lost or misplacement of the two components. On the other hand, the two components could be slidably and reversibly disposed to one another in a single horizontal movement providing the dried indicator reagent delivery unit is engaged in proper alignment above the test unit. In this particular instance, proper alignment of the two components may be achieved through the use of guide rails, or projections designed to align with recesses formed in the device or housing, additionally acting as an interconnection means for the two components.

The precise dimensions of the housing are not essential to the function of the assay apparatus, but in general, the apparatus will be of a size convenient for transport, manipulation, and assembly. The housing will generally have a length in the range of about 2 to 5 cm, preferably 3.5 cm. The width will be in the range of about 1 to 3 cm, preferably 2.5 cm. The height of the housing will be in the range of about 0.5 to 5 cm, preferably 1.3 cm.

FIG. 4 provides an exploded view of the apparatus 13 comprising the test unit 2 and the dried indicator reagent delivery unit 3, while FIG. 5 provides an enlarged vertical cross-sectional view of the fully assembled apparatus 13. The apparatus 13 of the present invention comprises two separate components in its fully assembled form, namely the test cartridge 14, which contains the test unit 2, and the dried indicator reagent delivery cap 15, which contains the dried indicator reagent delivery unit 3. The test cartridge 14 and the dried indicator reagent delivery cap 15 are designed to be connected to one another briefly during the assay protocol. The apparatus 13 is intended to be simple in design and construction, and can be manufactured using readily available materials.

As shown in FIG. 4, the test cartridge 14 of the apparatus 13 houses the test unit 2 which comprises both a top member 16 and a bottom member 17. The outer perimeter of the bottom member 17 has a slightly indented ridge 18 which allows it to be fitted and interconnected with the rim 19 bordering the top member 16 to form the assembled test cartridge 14. It will be appreciated by those skilled in the art that while the test cartridge 14 shown in FIGS. 4 and 5 has a rectangular shape, it is not limited to this particular configuration so long as it can be adapted to hold the absorbent material, or pad 20, in direct contact with the reaction membrane 21.

Contained within the top member 16 of the test cartridge 14 is a reservoir 22 which is in direct alignment with the exposed reaction membrane 21 of the test unit 2. The reservoir 22 (a) provides access to the reaction zone for introducing the fluid test sample, (b) provides operable attachment of the dried indicator reagent delivery cap 15 for introduction of the multifunctional buffer reagent, and (c) permits viewing of the test result on the reaction membrane 21 following removal of the dried indicator reagent delivery cap 15, i.e. detect the color, or fluorescence, or other signal, in the indicator zone(s). As depicted in the drawing, the upper surface surrounding the reservoir 22 is slightly curved and extended downwards so as to form a cup-like receptacle terminating at a portion of the reaction membrane 21. In this way, the amount of test sample introduced into the reservoir 22 cannot bypass any components of the apparatus 13. The configuration of the inner wall 23 and the dimensions of the reservoir 22 are selected so that the reservoir 22 can connect to and be in operable association with the dried indicator reagent delivery cap 15 during the assay protocol. Preferably, both the reservoir 22 and the dried indicator reagent delivery cap 15 have a funnel shape configuration. Thus, when the reservoir 22 and the dried indicator reagent delivery cap 15 are in the operating position and the multifunctional buffer is applied to the filter cap 15, this configuration will permit a suitable amount of the buffer to contact and pass through a small amount of surface area of the reaction membrane 21. Thus, by selectively matching the size of reservoir 22 with the dried indicator reagent delivery cap 15, the operation of the apparatus 13 can be simplified so that, for example, the multifunctional buffer 12 can be delivered to the reservoir 22 in a single step of the assay procedure.

According to the embodiment shown in FIGS. 4 and 5, the dried indicator reagent delivery cap 15 is detachable affixed to the reservoir 22 of the test cartridge 14 by means of a friction fit between the inner wall 23 of the reservoir 22 and the external wall 33' of the filter cap 15. Such other means for detachably affixing the dried indicator reagent delivery cap 15 to the test cartridge 14 can be used. In addition, the height of the external wall 33' of the dried indicator reagent delivery cap 15 is slightly less than the height of the inner wall 23 of the reservoir 22 so that when the filter cap 15 is affixed to the reservoir 22, the base 24 of the filter cap 15 terminates immediately above, but not touching, the reaction membrane 21. The dimensions of both the reservoir 22 and the dried indicator reagent delivery cap 15 can be varied without affecting the performance of the apparatus 13, although the following approximate dimensions have been determined as satisfactory: reservoir 22—1.5 cm top and bottom diameters and 0.6 cm deep; dried indicator reagent delivery cap 15—0.9 cm bottom diameter, 1.1 cm top diameter, and 0.5 cm deep.

As described above, the test unit of the present invention comprises a reaction membrane 21 and an absorbent pad 20, whereby the lower surface of the reaction membrane 21 is supported by the upper surface of the absorbent pad 20. The reaction membrane 21, which contains capture reagent capable of binding target analyte, essentially defines the reaction zone in which various specific binding reactions take place during the assay. As previously described, the reaction membrane 21 can be fabricated from a number of biologically inert, porous materials.

Positioned directly underneath the lower surface of the reaction membrane 21, and in fluid communication therewith, is an absorbent pad 20 defining the absorbent zone. In embodiments of the invention where ease of manufacture and reduced costs are desired, the entire upper surface of the absorbent pad 20 is typically immediately adjacent the lower surface of the reaction membrane 21. The test unit may optionally include a separating means between the reaction membrane 21 and the absorbent pad 20 which will generally be incapable of binding the target analyte of interest. According to the embodiment shown in FIG. 4, the separating means in the form of a spacer layer 25 isolates a portion of the reaction membrane 21 from the absorbent pad 20. Although not critical to the performance of the apparatus 13, the spacer layer 25 serves to secure the reaction membrane 21 in place and permit assay reagents to flow uniformly from the upper surface down to the lower surface of the assay apparatus 13.

The spacer layer 25 has an opening 26 defined by a rim 27 which has perimeter dimensions and a shape similar to the reaction membrane 21 thereby enabling the upper and lower surfaces of the reaction membrane 21 to be accessible when the membrane 21 and the spacer layer 25 are sealed together to form a press-fit piece. Referring to FIG. 4, which depicts one embodiment of the apparatus 13, a portion of the reaction membrane's 21 upper surface is fully exposed so that when the diagnostic assay is performed, the fluid test sample and the assay reagents can be added directly to the reaction membrane 21. The reaction membrane 21 is sized to completely cover the opening 26. Preferably the reaction membrane 21 will be the same shape as the opening 26, but sized slightly larger than the opening 26 so that it can be sealed to the lower surface of the spacer layer 25 at the periphery of the opening 26. However, the shape of the reaction membrane 21 and the shape of the opening 26 can differ and are not limited to the configuration shown in FIG. 4. Thus, in combination, the rim 27 surrounding the opening 26 and the exposed upper surface of the reaction membrane 21 essentially define a test region. Moreover, after the test cartridge 14 of the apparatus 13 is assembled, the absorbent pad 20 is still capable of contacting the lower surface of reaction membrane 21 located directly beneath the reaction membrane 21. The dimensions of the spacer layer 25 and the absorbent pad 20 are chosen to fit cooperatively within the base of the test cartridge 14, thereby ensuring that the absorbent pad 20 is in proper alignment and fluid communication with the lower surface of reaction membrane 21. Generally, the surface area of the upper surface of the absorbent pad 20 will usually be greater than that of the reaction membrane 21, but similar to that of the spacer layer 25.

The absorbent pad 20 is selected to have a capillary pore size so as to induce flow of the fluid test sample through the reaction membrane 21 without the use of external means. Thus, conveniently, the absorbent pad 20 serves to both promote and direct the flow of reagents through the reaction membrane 21. The absorbent pad 20 is of sufficient size and composition so that it is capable of absorbing excess sample, indicator reagent and buffer. The material from which the absorbent pad 20 is fabricated may be any permeable wettable material that is substantially inert to the assay reagents employed in the performance of an assay. The absorbent pad 20 will have essentially the same perimeter dimensions and shape as the spacer layer 25 which holds the reaction membrane 21. The precise thickness of the absorbent pad 20 is not essential to the function of the present invention, generally ranging from about 2 to 10 mm.

The second component of the apparatus is the funnel-shaped dried indicator reagent delivery cap 15 which readily accommodates a suitable amount of the multifunctional buffer needed to perform the assay in a single application. The dried indicator reagent delivery cap 15 comprises the dried indicator reagent delivery unit 3 and inner 28 and outer 29 sleeves being open-ended at both the top and bottom. The bottom opening 30, 30' of sleeves 28 and 29 is sized to achieve the flow rate desired for the assay in question. The opening of the sleeves can conveniently have a diameter in the range of 12.6 to 15.2 mm. Preferably the opening 30, 30' diameter is 9.5 mm.

In the assembled form, the dried indicator reagent delivery cap 15 comprises a funnel 31 having at its top outwardly extending flanges 32, 32' and depending sidewalls 33, 33'. The depending sidewalls 33 of the outer sleeve 29 terminate at base 24. The opening 30' at the base 24 allows a stream of fluid traveling through the funnel 31 to flow into the test cartridge 14. The dried indicator reagent delivery unit 3 of the present invention is securely held in the base 24 of dried indicator reagent delivery cap 15 by the inner 28 and outer sleeves 29 of the dried indicator reagent delivery cap 15. An inner collar 34, integrally formed at the base 24 of the outer sleeve 29, is capable of supporting the dried indicator reagent delivery unit 3 so that when the inner sleeve 28 is frictionally fitted inside the outer sleeve 29, the dried indicator reagent delivery unit 3 will be held permanently in place.

The dried indicator reagent delivery unit 3 comprises a filter medium impregnated with dried indicator reagent which defines the label zone. The dried indicator reagent is resolubilized and transported by the multifunctional buffer to the reaction membrane 21 following addition of the buffer to the dried indicator reagent delivery cap 15. The selection of the filter medium for the dried indicator reagent delivery unit 3 is not critical to the invention and can be any suitably absorbent, porous or capillary possessing material through which the multifunctional buffer and resolubilized indicator reagent may be transported by wicking action. The criteria of selection is that the material allow for the resolubilization and mixing of the dried indicator reagent upon addition of the multifunctional buffer, as well as initiate the transfer of the buffer and freshly dissolved indicator reagent to the reaction membrane 21 of the test unit 2.

For convenience of manipulation in using the apparatus 13, a handle 35 is secured to the extending flange 32 of the dried indicator reagent delivery cap 15 so that when the filter cap 15 is affixed to the reservoir 22, it extends slightly beyond the boundary of the reservoir 22 for ease of removal of the dried indicator reagent delivery cap 15 from the test cartridge 14.

Figure 7A:
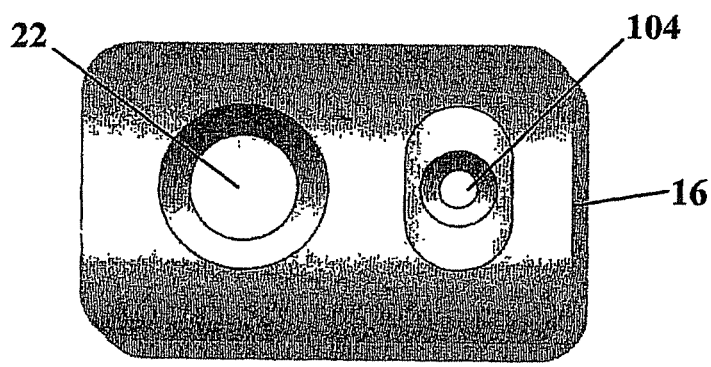
FIG. 7A is a diagrammatic illustration of a top plan view of the top member of a 2-reservoir test cartridge for receiving and analyzing a whole blood sample.
Figure 7B:
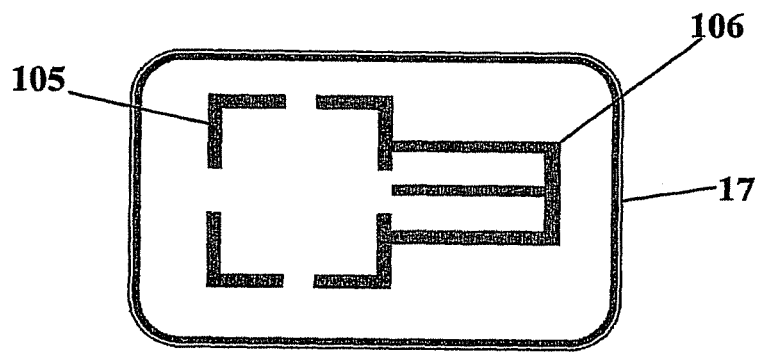
FIG. 7B is a diagrammatic illustration of a top plan view of the bottom member of a 2-reservoir test cartridge for receiving and analyzing a whole blood sample.

A representative example of a modified version of the test cartridge of the invention incorporating a blood separation zone in lateral fluid communication with the reaction zone for the detection of analyte in a whole blood sample is illustrated in FIGS. 7A and 7B.

As shown in FIG. 7A, the test cartridge is provided with a top member 16 constructed and adapted to fit snugly with a bottom member 17. In this particular embodiment, the top member 16 of the test cartridge defines a first opening or internal recess therethrough in the form of a reservoir 22. The reservoir 22 serves to (a) provide operable attachment of the dried indicator reagent delivery cap for introduction of the multifunctional buffer reagent, and (b) permit viewing of the test result on the membrane following removal of the dried indicator reagent delivery cap, i.e. detect the color or fluorescence, or other signal, in the indicator zone(s). Thus, the configuration and dimensions of the reservoir 22 are selected on the basis that it can be operably connected to the dried indicator reagent delivery cap to enable transient fluid communication between the label zone of the dried indicator reagent delivery unit and the reaction zone of the test unit.

Spaced a short lateral distance from the reservoir 22, the top member defines a second opening therethrough in the form of a reservoir 104 which may, as shown, have beveled sides, or may be in any shape or size or configuration of convenience which will sufficiently direct and provide access to the first end of the blood separation zone upon application of a whole blood sample. After introducing a whole blood sample to the reservoir 104 and allowing for a short incubation time to enable sufficient separation and migration of the RBC-free fluid along the blood separation zone to the reaction zone, the dried indicator reagent delivery cap is operably attached to the reservoir 22 to enable completion of the 2-step assay protocol so that a final determination for the presence of target analyte can be made.

As shown in FIG. 7B, the bottom member 17 of the test cartridge provides a first base structure 105 having a plurality of supporting walls which serve as a solid enclosure for the absorbent pad and thus, is configured to receive and hold the absorbent pad securely in place. Additionally provided is a second base structure 106 having a plurality of protruding columns of the same height which serves as an elevated support for the blood separation zone. The position of the second base structure 106 in relation to the first base structure 105, as well as its configuration, are such that when the blood separation zone is positioned within the bottom member 17, the blood separation zone is contiguous with and in direct planar horizontal alignment with the reaction zone. Although the base structure 106 depicted therein has a plurality of supporting columns and/or walls which serve to support the perimeter and centre of the blood separation zone, any number of configurations or strategies are possible as long as the blood separation zone is securely and correctly positioned in relation to the reaction zone when the test cartridge is fully assembled.

8.0 Methodology

In operation, the apparatus of the present invention broadly is used to determine the presence of target analyte in a fluid test sample, employing at least one capture reagent to form a detectible product on the reaction membrane as an indication that the analyte is present in the sample. The assay device and apparatus is particularly applicable to an immunoassay wherein the sample component is one component of an immunological pair including antigens, antibodies, or haptens. The immunological pair includes two components which immunologically bind to each other. Specific immunological pairs include antigens and their antibodies (monoclonal antibodies or affinity purified polyclonal antibodies, including fragments thereof), or biologically functional haptens and their antibodies. While monoclonal antibodies have known advantages over polyclonal antibodies, either type of immunological reagents can be used in accordance with the present invention. Thus, for simplicity of representation, the assay and device of the present invention will be described with respect to immunoassays using the antigen-antibody immunological pair. The fluid test sample is biologically derived, e.g. urine or serum, and the capture reagent and indicator reagent can comprise an antibody or antigen, depending on the analyte of interest and whether the sandwich or competitive technique is employed.

The immunoassays that use the analytical apparatus of the present invention can be very simple and fast, and can be qualitative or semi-quantitative. The analytical apparatus can be adapted for use in many different types of assays. For example, the target analyte can be a hormone, antibody, antigen, protein, etc. A non-inclusive list of possible target analytes is provided in U.S. Pat. No. 5,006,464 (Chu, et al.). The immunoassay format, will depend on the target analyte sought to be detected. Again, these are already known in the art. It will be appreciated by those skilled in the art that in order to maximize sensitivity for the detection of a particular target analyte, various components of the analytical device and/or assay procedure can be modified, such as the porosity, thickness and type of material used for the reaction membrane. The analytical device used in the assays essentially requires no sample manipulation and the entire assay protocol can be performed in less than 1 minute.

The assay device of the invention is contemplated to be used in any flow-through immunoassay procedure including competitive and preferably sandwich assays. As mentioned above, the reaction membrane is coated with a capture reagent, generally a specific antibody, or fragment thereof. Alternatively, if the target analyte is an antibody, the capture reagent may be a specific antigen. In either case, after capture reagent is applied to the membrane, it is preferred to fill any unoccupied binding sites with an inert protein to prevent nonspecific binding of any other assay reagent, such as the indicator reagent, to the membrane. In the present disclosure, the term "inert protein" means a protein which is immunologically unreactive toward any other component of the assay and which does not substantially bind nonspecifically to other proteins in the assay medium, with the understanding that the inert protein may well be immunologically reactive toward other materials which are not part of the assay of the invention. Representative non-limiting examples of suitable inert proteins are albumin and casein.

Referring first to a sandwich assay for the detection of antigen, the capture reagent will be a first antibody specific for the predetermined antigen and the indicator reagent will comprise a second antibody also specific for the predetermined antigen. The first antibody, preferably a monoclonal antibody or an affinity purified polyclonal antibody, is bound to the reaction membrane as the capture reagent. The first antibody is selected for its ability to recognize and bind to a specific epitopic site on the antigen of interest. The second antibody forming part of the indicator reagent will be selected on the basis that it will recognize and bind to an alternative epitopic site on the antigen of interest and thus, not interfere with the binding interaction of the first antibody with the antigen. One of skill in the art will also appreciate that the sandwich assay may also be performed by reversing the roles of the antigen and antibody. For example, the immobilized member of the immunological pair may be the antigen for the detection of an antibody of interest in the test sample utilizing a labeled anti-human antibody or Protein A as the indicator reagent.

Referring to FIGS. 4, 5 and 7, and using a fluid test sample other than whole blood, the method of the invention is carried out by directly depositing a volume of the fluid test sample onto the upper surface of the reaction membrane 21 by introduction through the opening in the reservoir 22. The amount of fluid test sample and multifunctional buffer reagent added to the assay apparatus 13 via the reservoir 22 may vary with different embodiments of the subject invention. In general, for a given specific embodiment, a predetermined and undiluted quantity of test sample will be added, while the multifunctional buffer reagent will normally be added in excess. A predetermined volume of sample is preferably added drop-wise, using a standard sterilized pipette, to the centre of the reservoir 22 so that uniform contact between the sample and the immobilized capture reagent is maintained. In a preferred embodiment of the invention, only a single drop of the fluid test sample is required to be added to the reservoir. As the fluid test sample is induced to flow through the absorbent pad 20 by capillary action, any free antigen that may be present in the test sample comes into contact with the antibody immobilized to the surface of the reaction membrane 21. The free antigen thus becomes immobilized by the antibody while the fluid test sample diffuses into the absorbent pad 20 underneath. The dried indicator reagent delivery cap 15 is subsequently connected and brought into operable association with the reservoir 22 of the test cartridge 14. A predetermined volume of multifunctional buffer may be measured by a marker in the reservoir 22, or preferably added dropwise, using a second standard sterilized pipette. The dropwise addition of the buffer reagent to the centre of the post filter-cap 15 should encourage uniform contact and saturation of the dried indicator reagent delivery unit 3 so that the dried indicator reagent will be fully resolubilized. Furthermore, the volume of buffer reagent should be sufficient to separate any unbound indicator reagent from the reaction membrane 21 after the specific binding interactions have occurred. As the stream of buffer reagent contacts and subsequently diffuses through the reaction membrane 21, unbound reactants are separated from the bound reactants. According to a preferred embodiment of the present invention a range of 10 to 15 drops of buffer can be added to the dried indicator reagent delivery cap 15. Upon addition of the multifunctional buffer and following resolubilization of the dried indicator reagent comprising labeled antibody, the labeled antibody is transported to the reaction membrane 21 by the buffer, where it will bind with any antigen that is bound by the immobilized antibody. Due to the volume and chemical properties of the multifunctional buffer, a separate washing step is not required in order to remove unbound labeled antibody. The presence of labeled antibody on the reaction membrane 21 is then determined as an indication of the presence of the target antigen in the sample. The binding reaction of the labeled antibody with the antigen produces a visually detectable signal indicative of a positive result that is easily observed directly following removal of the dried indicator reagent delivery cap 15.

The present invention is also applicable to the competitive binding technique for example, described in U.S. Pat. No. 4,366,241 (Tom, et al.). In such system for the detection of antigen in a fluid test sample, the corresponding member of the immunological pair, namely the antibody, is immobilized on the reaction membrane 21 surface. However, the binding member of the indicator reagent will be an authentic sample of the target antigen which has a comparable binding affinity for the antibody immobilized to the reaction membrane 21. After the fluid test sample is deposited on the reaction membrane 21, the presence of antigen, if any, and the ancillary antigen of the indicator reagent compete for sites of attachment to the antibody. Since the immobilized antibody is in limited supply, a competition is set up between the antigen in the sample and the labeled antigen. If there is no antigen present in the test sample, labeled antigen aggregates on the reaction membrane 21. Thus, the presence of color signifies a negative result due to the absence of detectable levels of antigen in the sample. If antigen is present, no color develops due to a reduction in the amount of labeled antigen bound by the immobilized antibody having binding sites already occupied by the target antigen, thus indicating a positive result. Accordingly, the signal emitted from the label is inversely proportional to the amount of antigen in the sample. Moreover, as with the sandwich assay, the competitive binding assay may be performed by reversing the roles of the antigen and antibody. For example, the immobilized member of the immunological pair may be the antigen for the detection of an antibody of interest in the test sample which competes with labeled antibody.

As a further consideration, this system could be expanded to include the simultaneous detection of two or more analytes of interest in a fluid test sample by using a corresponding number of immobilized immunological reagents on the reaction zone. As an example, a first antibody may be selected that is reactive with a particular subunit of a number of different antibodies. If a second antibody is specific for a subunit of one antigen only, such second antibody can be used as the immobilized antibody and a single labeled first antibody can be used as the universal labeled antibody for antigen of interest. On the other hand, two different types of immobilized antibody may be employed if it is expected that antigen capable of being recognized by its appropriate binding partner is likely to present in a fluid test sample, e.g. anti-HCV antibody and anti-HIV antibody found in a co-infected patient sample.

In the case of analyzing a whole blood sample, the method of the invention is essentially identical to that described above with the exception that a volume of the sample is directly deposited into the reservoir 104 which allows access to and direct contact with the first end of the blood separation zone through the opening defined therein (refer also to FIG. 7A). The amount of the whole blood sample applied to the reservoir 104 and the amount of multifunctional buffer reagent added to the reservoir 22 may vary with different embodiments of the subject invention. In general, for a given specific embodiment, a predetermined and undiluted quantity of test sample will be added, while the multifunctional buffer reagent will normally be added in excess. A predetermined volume of the sample is preferably added dropwise, using a standard sterilized pipette, to the centre of the reservoir 104 so that uniform contact between the sample and the blood separation zone is ensured.

In a preferred embodiment of the invention, only two drops of the whole blood sample are required to be added to the reservoir 104. Following a short incubation period, the RBC-free portion of the whole blood sample, including any analyte, migrates in a lateral direction along the blood separation zone until it arrives at the reaction membrane 21. As the RBC-free fluid test sample is induced to flow through the absorbent pad 20 by capillary action, any free antigen that may be present in the test sample comes into contact with the antibody immobilized to the surface of the reaction membrane 21. The free antigen thus becomes bound by the antibody while the fluid test sample, along with non-essential components, diffuses into the absorbent pad 20 underneath. The dried indicator reagent delivery cap 15 is subsequently connected and brought into operable association with the reservoir 22 of the test cartridge 14. A predetermined volume of multifunctional buffer may be measured by a marker in the reservoir 22, or preferably added dropwise, using a second standard sterilized pipette. The dropwise addition of the buffer reagent to the centre of the post filter-cap 15 should encourage uniform contact and saturation of the dried indicator reagent delivery unit 3 so that the dried indicator reagent will be fully resolubilized. Furthermore, the volume of buffer reagent should be sufficient to separate any unbound indicator reagent from the reaction membrane 21 after the specific binding interactions have occurred. As the stream of buffer reagent contacts and subsequently diffuses through the reaction membrane 21, unbound reactants are separated from the bound reactants. According to a preferred embodiment of the present invention a range of 10 to 15 drops of buffer can be added to the dried indicator reagent delivery cap 15. Upon addition of the multifunctional buffer and following resolubilization of the dried indicator reagent comprising labeled antibody, the labeled antibody is transported to the reaction membrane 21 by the buffer, where it will complex with any antigen that is bound by the immobilized antibody. Due to the volume and chemical properties of the multifunctional buffer, a separate washing step is not required in order to remove unbound labeled antibody. The presence of labeled antibody on the reaction membrane 21 is then determined as an indication of the presence of the target antigen in the sample. The binding reaction of the labeled antibody with the antigen produces a visually detectable signal indicative of a positive result that is easily observed following removal of the dried indicator reagent delivery cap 15.

9.0 Test Kit

According to the invention, kits may be produced which include the rapid assay device, the multifunctional buffer, as well as instructions describing the assay protocol for determining the presence of a target analyte in a fluid test sample. The diagnostic device of the present invention, which incorporates the test unit and dried indicator reagent delivery unit, will typically be packaged in the form of a diagnostic kit for use in the detection of the target analyte of interest. The kit will normally include the flow-through assay device, preferably housed in a suitable container, the multifunctional buffer, disposable plastic pipettes and instructions describing the method for carrying out the assay protocol. Depending on the type of assay performed, i.e. sandwich or competitive, and the target analyte to be determined in the fluid test sample, the instructions will also include the relative amounts of test sample and multifunctional buffer to be added to the test unit and dried indicator reagent delivery unit, respectively. In addition, the time periods required involving the sequential addition of the sample and buffer, as well as that the time required for the generation of a result will be included.

The preferred kit of the present invention uses the flow-through diagnostic device as described and shown in FIGS. 1 to 3. Preferably, the flow-through diagnostic device is housed within a suitable container that can be included in the test kit comprising two detachable components, each component separately containing the test unit and the dried indicator reagent delivery unit, which are arranged in a vertically and spatially distinct format. In particular, the design of the container should allow the test unit and dried indicator reagent delivery unit to be operably connected to one another so that the reaction zone and the label zone can be placed in transient fluid communication with one another during the assay protocol in a single movement. The container housing the test unit should be capable of maintaining the layers of the test unit under compression so as to provide continuous and uniform contact therebetween so that liquid will flow uniformly through the apparatus. FIGS. 4, 5 and 7 provides a representative example of the type of container that can be included in a test kit which incorporates the flow-through device of the present invention.

The invention will be further understood from the following non-limiting examples. The following examples are provided to describe in detail some of the representative, presently preferred methods and materials of the invention. These examples are provided for purposes of illustration of the inventive concepts, and are not intended to limit the scope of the invention as defined by the appended claims.

10.0 Examples

The foregoing is a general description of the apparatus, method and reagents of the invention. A sandwich-type reaction may be performed for the detection of *Helicobacter pylori*. Thus, by way of an example provided below, the capture reagent is a solution of *Helicobacter pylori* which is applied to the reaction membrane of the test unit. Although dye sols, gold sols or coloured latex particles may be linked to Protein A to form the indicator reagent, the preferred visual label utilized in the example assay will be colloidal gold particles. Using an apparatus comprising the test unit and dried indicator reagent delivery unit, such as the one illustrated in FIGS. 4 and 5, and by performing the 2-step rapid assay of the present invention, a determination of antibody against *Helicobacter pylori* in a serum test sample can be made in less than three minutes.

10.1 Preparation of the Diagnostic Assay Apparatus

The apparatus 13, illustrated in FIGS. 4 and 5 comprising a test cartridge 14 and dried indicator reagent delivery cap 15, represents a suitable container to house the test unit 2 and dried indicator reagent delivery unit 3 of the present invention.

A. Test Cartridge

The test cartridge, which houses the test unit of the rapid test device, is made of clean technical grade white polypropylene plastic and has a top 16 and bottom 17 component. Both are made in synchronized 16 cavity mold, precisely engineered to allow a snugly fitting tight seal when the two components are pressed together. The components are supplied as individual casings by Top View International Limited, Hong Kong, and are assembled at the manufacturing plant of MedMira Laboratories, Halifax, Canada. These components meet the following criteria:

Appearance—a clear, white smooth texture of the plastic.

A snug fit to produce a leak-proof housing to ensure safe containment of all applied liquids.

Consistency of dimensions to specifications of 2.5 cm width, 3.5 cm length, and 1.3 cm height.

Consistency of dimensions of the reservoir 22 opening of 1.6 cm in diameter and a formed cylinder depth of 0.5 cm.

Consistency in the location of the reservoir 22 in the top component of the test cartridge 14.

B. Reaction Zone

The material used for the reaction zone is a membrane 21 such as nitrocellulose having an average pore size of 0.45 microns (Whatman, England) and cut to 12 mm×12 mm. The membrane 21 is 0.2 mm thick paper-backed nitrocellulose and specially treated for enhanced protein binding. Certified specifications given by the manufacturer (Whatman, England) include a binding capacity of 80-90 mg protein/$cm^2$, a water flow rate of 6 mL/min/$cm^2$ and a bubble point of 3.5 bar. The reaction membrane 21 is prepared having two immunoreactive test sites, namely a test zone and a control zone, each zone produced in the shape of a distinct vertical line. The control line and the test line are positioned perpendicular to, but not touching, one another to provide a clear differentiation between the two. The test zone of the membrane is prepared by applying a solution of *Helicobacter pylori* in phosphate buffer (pH 7 to 9.5) using a printer device (BioJet Quanti 3000 dispenser). The control zone is similarly prepared by applying a mixture of a specially calibrated antigen preparation that binds to all classes of IgG antibodies ordinarily present in a biological fluid test sample regardless of *Helicobacter pylori* IgG antibody status, and thus serves as a control zone. After the membrane is dried at room temperature for 10 minutes, it is treated with a solution of 1% bovine serum albumin in 0.1 M sodium phosphate buffer and allowed to completely dry at ambient temperature for approximately 24 hours.

C. Optional Spacer Layer

A spacer layer 25 supporting the reaction membrane 21 may be produced by securing the outer perimeter of the upper surface of the reaction membrane 21 to the lower surface of the spacer layer 25 such that the upper surface of the reaction membrane 21 is exposed through an opening of the spacer layer 25. The upper surface of the reaction membrane 21 is sealed to the lower surface of the spacer layer with a fluid-resistant adhesive so as to form an impermeable seal between the rim 27 of the spacer layer 25, defining the opening 26, and the unexposed upper surface of the reaction membrane 21. This arrangement helps to promote the flow of fluids in a downward, as opposed to lateral, direction through the reaction membrane 21 and into the absorbent pad 20 below. The spacer layer 25 may be purchased with water-soluble adhesive already adhered to the lower surface, or the adhesive may be applied during the manufacturing process. The spacer layer 25 is a polystyrene material insert with a brown paperback double-sided tape (Halifax Folding Company, Nova Scotia, Canada). The reaction membrane 21 is secured to the spacer layer 25 by the double-sided tape. The assembled spacer layer 25 is approximately 29.0 mm×20.5 mm in area and 1.0 mm in thickness and is positioned on the upper surface of the absorbent pad 20 which sits in the base of the test cartridge 14 as shown in FIGS. 4 and 5.

D. Absorbent Zone

The absorbent zone comprises a pad 20 placed directly beneath the reaction membrane 21 and securely inside the bottom member 17 of the test cartridge 14. The pad 20 is composed of thickened compressed cellulose acetate with a porosity of 40 mL/min (Filtrona, Richmond Inc., Richmond, Va.). It is made of synthetic fibers without the use of resins or adhesives and provides an excellent level of aqueous fluid compatibility. Void space is specified at 80 to 85% and absorption of liquids at 6 times the dry unit weight and up to 90% of the total void volume. It is resistant to pH in the range of 2.5 to 9.5. The pad 20 is die cut to a specification of 2.2 cm width, 3.2 cm length and 0.5 cm height. The pad 20 fits securely into the bottom member 17 of the test cartridge 14 so as to create a compressed composite of the reaction membrane 21 with the absorbent pad 20 to ensure a continuum of fluid communication between the porous materials for enhanced hydrodynamics and complete absorption when test samples are applied to the reaction membrane 21.

E. Dried Indicator Reagent Delivery Cap

The dried indicator reagent delivery cap 15, which houses the dried indicator reagent delivery unit 3 of the rapid test apparatus 13, is comprised of an outer funnel sleeve 29 having an internal collar 34 at its base, an inner funnel sleeve 28 having a handle 35 extending therefrom, and the dried indicator reagent delivery unit 3. The funnel sleeves 28, 29 and the handle 35 are molded from a plastic material. One preferred plastic material is polystyrene resin (Fouzhou Chimoplus Chemical Company Ltd., China). The outer 29 and inner 28 funnel sleeves are cylindrical in shape with an outside diameter of 15.0 mm and 12.5 mm, respectively and the assembled cap 15 fits snugly into the reservoir 22 of the test cartridge 14. The dried indicator reagent delivery cap 15 is designed to be connected to the reservoir 22 of the test cartridge 14 following post-application of the test sample to the reservoir 22, and removed shortly after the multifunctional buffer has been added and diffused through the dried indicator reagent delivery unit 3 of the filter cap 15. In the assembled form, the volume capacity of the dried indicator reagent delivery cap 15 is about 0.5 mL.

The label zone of the dried indicator reagent delivery unit 3 is comprised of one filter layer permeated with indicator reagent that will be in direct fluid communication with the reaction zone of the test unit 2 to improve the subsequent reactivity between the antibodies of the colloidal gold conjugate and the antigen-coated reaction membrane 21. The filter is comprised of glass micro fiber with OVA binder (Whatman, GF/AVA) which is white and has a basis weight of 48 g/m$^2$, a thickness of 0.303 mm, a flow rate of 150 s/1.5 cm, dry tensile of 640 g/1.5 cm, wet tensile of 324 g/1.5 cm and a porosity of 3 sec/100 mL/in$^2$. Once assembled, the freeze-dried colloidal gold conjugate is reconstituted with a solution comprising 0.1-0.15 mL of PBS buffer (0.6-0.7 mM potassium chloride, 0.03M sodium chloride, 2-2.1 mM di-sodium hydrogen orthophosphate anhydrous, 0.3-0.4 mM potassium phosphate mono) containing 10% sugar. The colloidal gold conjugate solution is dispensed (0.1 to 0.15 mL) onto each filter and then dried at a temperature of 37 to 40° C. The filter layer is die cut according to the following specifications: thickness, 790 to 830 microns; porosity, 1.6 to 2.0 s/100 mL/in$^2$; tensile strength 14.5 N/55 mm; flow rate, 67 s/7.5 cm; absorbancy, 76.4%; pore size, 4.3 microns; wicking, 1.00 min:sec; and diameter, 0.42 mm.

10.2 Inspection on Protein A (PA)

Formulation

Sodium Chloride

10% in DDI water

BSA

1% BSA in DDI water pH 5.00 to 9.00 (optimum 6.00).

Colloidal gold

Prepared up to the pH step.

Stock-solution of the Labeling Material

Original concentration diluted in DDI to a final concentration of 0.1-2 mg/mL (optimum 0.1 mg/mL)

Procedure

Prepare a 9 serial dilution Protein A (PA).

To the PA, dilution add the colloidal gold already pH adjusted in a 1:10 ratio (e.g. to 0.1 mL of PA dilution add 1 mL of colloidal gold).

Incubate for 10 minutes.

To each dilution tubes add 8-10% of sodium chloride to a final concentration of 1% (optimum 0.9%).

Incubate for 5 minutes.

To each tube again add 0.07-0.1% of bovine serum albumin to a final concentration of 0.1% (optimum 0.08%).

Read the absorbance at 520 nm.

The correct concentration of protein is the minimal amount that will inhibit flocculation.

| Conc. (µg) | Absorbance 1 | Absorbance 2 | Average |
|---|---|---|---|
| 0 | 0.313 | 0.314 | 0.314 |
| 2 | 0.524 | 0.524 | 0.524 |
| 3 | 0.533 | 0.532 | 0.533 |
| 4 | 0.533 | 0.533 | 0.533 |
| 5 | 0.540 | 0.540 | 0.540 |
| 6 | 0.575 | 0.571 | 0.573 |
| 7 | 0.580 | 0.580 | 0.580 |
| 8 | 0.576 | 0.583 | 0.580 |
| 9 | 0.576 | 0.576 | 576 |

Hughes D. A & J. E. Beesley (1998) Preparation of Colloidal Gold Probes in (ed) J. D. Pound. Methods in Molecular Biology vol 80: Immunochemical Protocols, 2$^{nd}$ edition. Humana Press Inc., Totowa, N.J.

10.3 Preparation of Colloidal Gold Conjugate

| Materials | |
|---|---|
| Sodium Citrate | 0.3 mM in DDI water |
| BSA | 1% BSA in DDI water, pH 5.00 to 9.00 |
| PEG | 1% polyethylene glycol (MW 15,000 to 20,000) in DDI water, pH to 6.00 |
| Phosphate Buffer | mix 0.04M (in DI water) of $NaH_2PO_4$ into 0.07M (in water) $KH_2PO_4$ in a 1:4.4 ratio; pH to 6.00 |
| Protein A in Hepes Buffer | Protein A in Hepes buffer (0.025M Hepes and 0.25 mM Thimerosal pH 7.00 in ODI water) to give a final concentration on 1 mg/mL. |
| Borate buffer | 0.05M of sodium borate in DDI water pH 8.50 |

Resuspending Buffer
   8 mM di-sodium hydrogen orthophosphate anhydrous
   1% bovine serum albumin
   3 mM sodium azide
   0.02% polyethylene glycol
   0.14-0.16M sodium chloride
   1.5 mM potassium dihydrogen orthophosphate
   2.7 mM potassium chloride
   4.3 mM tri-sodium orthophosphate
   Mix the above ingredients in 1000 mL of DDI water, pH 7.30 to 7.50.
Procedure
   Add 1% of tetrachloroauric acid to water for a final concentration of 0.01%.
   Let solution reach a hard boiling point.
   Add 15 mL of 0.3 mM sodium citrate on a reflux for 30 minutes.
   Remove the flask and allow the contents to cool to around 40° C. or lower.
   Add 60 mL of phosphate buffer (mix 0.04M (in DI water) of NaH2PO4 into 0.07M (in water) KH2PO4 in a 1:4.4 ratio; pH to 6.00) or 50 mM of borate buffer (pH 8.50); adjust pH of the colloidal gold to 6.00-9.00 (optimal is 6.00), if the pH is too low, add drops of 2 mM K2CO3.
   A portion of the solution is removed to perform an aggregation test to know the concentration of the ligand to add to the gold solution.
   Add Protein A with a final concentration of 5-9 ug/mL+ 5°/0 (optimum 6+0.3=6.3 ug/mL)

$$\frac{[Final\ PA + 5\%](mg/L) \times total\ volume\ in\ flask\ (L)}{[Initial\ PA](mg/mL)}$$

i.e. Total volume=500 mL CG and dH2O+15 mL sodium citrate+60 mL phosphate buffer- 3 mL test for pH = 572 mL = 0.572 $L$ $$\frac{(6+0.3)\ mg/L \times 0.572\ L}{1\ mg/mL} = 3.60\ mL\ Protein\ A\ to\ be\ added$$

The solution is allowed to proceed for 15-30 minutes (optimum 20 minutes).
The absorption of the ligand is stop by adding 10% bovine serum albumin pH 5.00 to 9.00 final concentration of 0.1% stir for 5-15 minutes (optimum 10 minutes).
The labeled colloidal gold was centrifuged at a speed of 46,500 g (20,000 rpm) at a temperature of 4-5 C for 50 to 80 minutes.

Aspiration and Re-Suspension
   Aspirate the supernatant with the help of a vacuum flask, taking care not to disturb the pellet. Resuspend in re-suspending buffer (or PBS-BSA) to a final optical density of 1.180 to 4.500 (optimum 2.000) at 520 nm.
Lyophilization Process
   After the appropriate optical density reach, the solution was filled in 0.6 mL aliquots into a 3 mL glass vials. Slotted stoppers (1-mm in diameter) were inserted halfway into the vials and transferred into the lyophilizer shelves. A temperature of −40 C was maintained for about 5 hours. The primary drying was carried out at a vacuum of less than 100 mTorr with a shelf temperature of −30 C for about 3 hours and a condenser temperature of less than −80 C. Followed is a shelf temperature of −10 C for about 5 hours then a shelf temperature of 0 C, vacuum of 0 mTorr for about 2 hours. A secondary drying is carry on at +20 C for about 4 hours. At the end of the process, the vials were seal under vacuum with the slotted stoppers. The product was then removed from the shelves and a functional test was performed to assure the quality of the product. Samples were kept for later reference.

10.4 Stabilization of Colloidal Gold Conjugate

Procedure
   Prepare 1%, 2%, 5% and 10% sucrose in PBS solution, pH 7.0-7.5.
   Reconstitute freeze-dried colloidal gold conjugate with a) 5 drops (150 µL) b) 10 drops (350 µL) and c) 15 drops (650 µL) with each percentage of sucrose.
   Apply 5 drops (150 µL) of each reconstitution to the filter medium.

| | Result | | | |
|---|---|---|---|---|
| Specimen | 1% | 2% | 5% | 10% |
| Control line | 2+ | 2+ | 2+ | 3+ |
| Positive control | 1+ | 1+ | 1+ | 2+/3+ |
| Negative control | neg | neg | neg | neg |

10.5 Preparation of the Dried Indicator Reagent Delivery Unit

One of the goals in diagnostic testing is to develop a test device that requires few manipulative steps. Therefore, by associating the indicator reagent with the filter medium of the dried indicator reagent delivery unit 3, it is possible to eliminate extra steps in which the reagents are added separately to the diagnostic device during the assay protocol.

Materials
   Colloidal gold conjugate, Prepared and previously freeze-dried as described above.
   Sugar, e.g. trehalose, lactose, sucrose, glucose, maltose, mannose, fructose, etc.
Procedure
   Reconstitute the freeze-dried colloidal gold with 0.1-0.15 mL of PBS buffer (0.6-0.7 mM potassium chloride, 0.03M Sodium chloride, 2-2.1 mM di-sodium hydrogen orthophosphate anhydrous, 0.3-0.4 mM potassium phosphate mono) containing 10% sucrose.
   Dispense 0.1 to 0.15 mL of colloidal gold solution onto each filter.
   Let the filter dry completely at 37-40 C.

10.6 Preparation of the Multifunctional Buffer
Formulation
- 0.01-0.1M EDTA
- 0.02M Sodium azide
- 0.05-0.1M Sodium chloride
- 6 mM di-sodium hydrogen orthophosphate anhydrous
- 0.1-0.25 mM Thimerosal
- 0.05-0.1% Triton®X-100
- 0.02-0.03M Trizma hydrochloride
- 0.2-0.3% Tween-20
- 0.5-2.5% PVP-40

Procedure

Add all ingredients together (0.01-0.1M EDTA, 0.02M sodium azide, 0.05

0.1M sodium chloride, 6 mM di-sodium hydrogen orthophosphate anhydrous, 0.1-0.25 mM Thimerosal, 0.05-0.1% Triton®X-100, 0.02-0.03M Trizma hydrochloride, 0.2-0.3% Tween-20, 0.5-2.5% PVP-40).

Fill up with DDI water.

Adjust the pH to 7.00 to 10.00.

10.6 Assay Protocol

Serum or Plasma Sample

Using a clean pipette, 1 drop of a serum or plasma sample was added to the centre of the reaction membrane and the sample allowed to absorb completely through the membrane and into the absorbent material pad. The dried indicator reagent delivery cap was connected to the reservoir of the test cartridge so that the dried indicator reagent delivery unit was in fluid communication with the test unit. Ten to fifteen drops of the multifunctional buffer were subsequently added to the funnel of the dried indicator reagent delivery cap. After a brief incubation, about 1 minute, during which time the resolubilized colloidal gold conjugate was drawn through the dried indicator reagent delivery unit, the dried indicator reagent delivery cap was removed from the test cartridge. A distinct colored line(s), one vertical control line and one test line, developed in the centre of the reaction membrane indicating the presence of *Helicobacter pylori* in the test sample. The results of the assay were revealed in about three (3) minutes.

What is claimed is:

1. A method for determining the presence or absence of a target analyte in a fluid test sample, the method comprising the steps of:

applying the fluid test sample to a reaction zone of a test unit, whereby the fluid test sample flows downwardly or vertically through the reaction zone, the reaction zone containing an immobilized capture reagent that binds the target analyte in the deposited fluid test sample to form a two-membered complex of a specific binding interaction;

allowing the fluid test sample to flow downwardly or vertically through the reaction zone into an absorbent zone in vertical communication with the reaction zone, the absorbent zone comprising an absorbent material positioned underneath the reaction zone for facilitating the downward or vertical flow of the fluid test sample through the reaction zone so as to concentrate the two-membered complex in the reaction zone;

affixing a post filter unit to the test unit, such that a label zone of the post-filter unit and the reaction zone of the test unit are proximally disposed, so as to be in transient fluid communication with one another to thereby allow direct downward or vertical fluid flow of a resolubilized dried indicator agent in the label zone to the reaction zone;

applying a buffer reagent to the post-filter unit to resolubilize the dried indicator reagent after the fluid test sample is applied to the reaction zone and after the post-filter unit is affixed to the test unit;

allowing the resolubilized indicator reagent to flow downwardly or vertically through the reaction zone and into the absorbent zone to bind with the two-membered complex concentrated in the reaction zone, with any unbound reactants being washed from the reaction zone into the absorbent zone; and removing the post-filter unit from the test unit subsequent to the application of the buffer reagent to the label zone and detecting the binding of the resolubilized indicator reagent with the two-membered complex, wherein the indicator reagent is selected from metal complex labels, radioactive labels, fluorescent labels, and chemiluminescent labels.

2. The method according to claim 1, wherein the buffer reagent is a multifunctional buffer comprising: a biological buffer to maintain the pH between 7.0 to 10.0; at least one surfactant to reduce non-specific binding of assay reagents while simultaneously avoiding inhibition of a specific binding interaction; a high molecular weight polymer as a dispersing and suspending reagent having a molecular weight in a range of from about $2 \times 10^2$ to about $2 \times 10^6$ D; a pH stabilizer to maintain the pH of the multifunctional buffer within a range of about pH 7.0 to 10.0; an ionic salt to reduce non-specific binding of antibodies; at least one preservative to reduce bacterial and microbial growth; and a calcium chelator to prevent a whole blood test sample from clotting; wherein the biological buffer, the surfactant, the high molecular weight polymer, the pH stabilizer, the ionic salt, the preservative and the calcium chelator are all in effective concentrations.

3. The method according to claim 1, wherein the specific binding interaction is an antibody-antigen interaction.

4. The method according to claim 3, wherein the target analyte is an antigen and the capture reagent is a monoclonal antibody or an affinity purified polyclonal antibody for the antigen.

5. The method according to claim 1, wherein the indicator reagent is capable of binding to a target analyte at a site which does not interfere with the specific binding interaction between the target analyte and the capture reagent.

6. The method according to claim 1, wherein the indicator reagent is capable of binding to the capture reagent at a site which interferes with the specific binding interaction between the target analyte and the capture reagent.

7. The method according to claim 1, wherein the reaction zone is comprised of a material which has a pore size permitting separation and filtration of unbound components from the fluid test sample and a thickness which permits an adequate amount of capture reagent to be immobilized thereto.

8. The method according to claim 7, wherein the material has a pore size ranging from about 0.1 to 12.0 microns.

9. The method according to claim 8, wherein the material has a pore size ranging from about 0.2 to 0.8 microns.

10. The method according to claim 7, wherein the thickness of the material ranges from about 0.05 mm to about 30 mm.

11. The method according to claim 10, wherein the thickness of the material ranges from about 0.1 to about 1.0 mm.

12. The method according to claim 7, wherein the material is a nitrocellulose membrane.

13. The method according to claim 1, wherein the reaction zone contains two or more different capture reagents immobilized thereto in discernable and separate areas so that multiple target analytes in a single fluid test sample can be analyzed simultaneously.

14. The method according to claim 1, wherein the reaction zone further comprises an immobilized control reagent in a discernable and separate area from the capture reagent.

15. The method according to claim 1, wherein the absorbent zone is separated from the reaction zone by an intervening spacer layer having one or more openings defined therein to permit fluid communication between the reaction zone and the absorbent zone.

16. The method according to claim 15, wherein the spacer layer is a rigid or semi-rigid fluid-resistant material.

17. The method according to claim 1, wherein the absorbent zone comprises one or more layers of a material which is capable of wicking fluid by capillary action and absorbing a substantial volume of fluid.

18. The method according to claim 17, wherein two or more layers comprise identical or different materials.

19. The method according to claim 17, wherein the material is cellulose acetate.

20. The method according to claim 1, wherein the label zone comprises a filter material having a pore size capable of allowing dried indicator reagent to be effectively resolubilized by buffer reagent and transferred to the reaction zone by laminar fluid flow.

21. The method according to claim 20, wherein the filter material is glass fiber material.

\* \* \* \* \*